(12) United States Patent
Denutte et al.

(10) Patent No.: US 8,524,650 B2
(45) Date of Patent: Sep. 3, 2013

(54) ENCAPSULATES

(75) Inventors: Hugo Robert Germain Denutte, Hofstade (BE); Jonathan Richard Clare, Newcastle (GB); Javier Medina, Newcastle (GB); Philip Andrew Cunningham, Vossem (BE); Johan Smets, Lubbeek (BE); Laura Orlandini, Puurs (BE)

(73) Assignee: The Procter & Gamble Company, Cincinnati, OH (US)

( * ) Notice: Subject to any disclaimer, the term of this patent is extended or adjusted under 35 U.S.C. 154(b) by 278 days.

(21) Appl. No.: 12/969,631

(22) Filed: Dec. 16, 2010

(65) Prior Publication Data

US 2011/0152146 A1 Jun. 23, 2011

Related U.S. Application Data

(60) Provisional application No. 61/287,795, filed on Dec. 18, 2009.

(51) Int. Cl.
*C11D 3/50* (2006.01)

(52) U.S. Cl.
USPC .............................................................. 512/4

(58) Field of Classification Search
USPC .............................................................. 512/4
See application file for complete search history.

(56) References Cited

U.S. PATENT DOCUMENTS

| | | | |
|---|---|---|---|
| 3,594,328 A | 7/1971 | Luzius | |
| 3,812,011 A | 5/1974 | Okada et al. | |
| 4,234,627 A | 11/1980 | Schilling | |
| 4,317,881 A | 3/1982 | Yagi et al. | |
| 4,378,923 A | 4/1983 | Takei | |
| 4,418,144 A | 11/1983 | Okada et al. | |
| 4,430,243 A | 2/1984 | Bragg | |
| 4,514,461 A | 4/1985 | Woo | |
| 4,515,705 A | 5/1985 | Moeddel | |
| 4,537,706 A | 8/1985 | Severson, Jr. | |
| 4,537,707 A | 8/1985 | Severson, Jr. | |
| 4,539,135 A | 9/1985 | Ramachandran et al. | |
| 4,540,721 A | 9/1985 | Staller | |
| 4,550,862 A | 11/1985 | Barker et al. | |
| 4,561,998 A | 12/1985 | Wertz et al. | |
| 4,597,898 A | 7/1986 | Vander Meer | |
| 4,719,043 A | 1/1988 | Schaper et al. | |
| RE32,713 E | 7/1988 | Woo | |
| 4,882,220 A | 11/1989 | Ono et al. | |
| 4,911,852 A | 3/1990 | Coffindaffer et al. | |
| 4,917,920 A | 4/1990 | Ono et al. | |
| 4,968,451 A | 11/1990 | Scheibel et al. | |
| 4,973,422 A | 11/1990 | Schmidt | |
| 5,486,303 A | 1/1996 | Capeci et al. | |
| 5,489,392 A | 2/1996 | Capeci et al. | |
| 5,506,201 A | 4/1996 | McDermott et al. | |
| 5,516,448 A | 5/1996 | Capeci et al. | |
| 5,552,378 A | 9/1996 | Trinh et al. | |
| 5,565,145 A | 10/1996 | Watson et al. | |
| 5,565,422 A | 10/1996 | Del Greco et al. | |
| 5,569,645 A | 10/1996 | Dinniwell et al. | |
| 5,574,005 A | 11/1996 | Welch et al. | |
| 5,576,282 A | 11/1996 | Miracle et al. | |
| 5,595,967 A | 1/1997 | Miracle et al. | |
| 5,597,936 A | 1/1997 | Perkins et al. | |
| 5,651,976 A | 7/1997 | Price et al. | |
| 5,691,297 A | 11/1997 | Nassano et al. | |
| 5,858,959 A | 1/1999 | Surutzidis et al. | |
| 5,879,584 A | 3/1999 | Bianchetti et al. | |
| 5,929,022 A | 7/1999 | Velazquez | |
| 6,024,943 A | 2/2000 | Ness et al. | |
| 6,042,792 A | 3/2000 | Shefer et al. | |
| 6,048,830 A | 4/2000 | Gallon et al. | |
| 6,051,540 A | 4/2000 | Shefer et al. | |
| 6,106,875 A | 8/2000 | Soper et al. | |
| 6,200,949 B1 | 3/2001 | Reijmer et al. | |
| 6,225,464 B1 | 5/2001 | Hiler, II et al. | |
| 6,245,732 B1 | 6/2001 | Gallon et al. | |
| 6,255,268 B1 | 7/2001 | Counts | |
| 6,294,514 B1 | 9/2001 | Welling | |
| 6,306,812 B1 | 10/2001 | Perkins et al. | |
| 6,326,348 B1 | 12/2001 | Vinson et al. | |
| 6,376,445 B1 | 4/2002 | Bettiol et al. | |
| 6,458,754 B1 | 10/2002 | Velazquez et al. | |
| 6,531,444 B1 | 3/2003 | Shefer et al. | |
| 6,645,479 B1 | 11/2003 | Shefer et al. | |
| 6,869,923 B1 | 3/2005 | Cunningham et al. | |
| 7,119,060 B2 | 10/2006 | Shefer et al. | |
| 7,169,741 B2 | 1/2007 | Barry et al. | |
| 7,297,674 B2 | 11/2007 | Hines | |
| 7,713,922 B2 | 5/2010 | Duprey et al. | |
| 7,781,392 B2 | 8/2010 | Perring et al. | |
| 2003/0125222 A1 | 7/2003 | Jahns et al. | |
| 2003/0158344 A1 | 8/2003 | Rodriques et al. | |
| 2003/0165692 A1 | 9/2003 | Koch et al. | |
| 2003/0195133 A1 | 10/2003 | Shefer et al. | |
| 2003/0203829 A1 | 10/2003 | Shefer et al. | |
| 2003/0215417 A1 | 11/2003 | Uchiyama et al. | |

(Continued)

FOREIGN PATENT DOCUMENTS

| | | |
|---|---|---|
| WO | WO 00/32601 A2 | 6/2000 |
| WO | WO 03/015736 A2 | 2/2003 |
| WO | WO 2008016637 A1 * | 2/2008 |

OTHER PUBLICATIONS

International Search Report; International Application No. PCT/US2010/060662; date of mailing Mar. 18, 2011; 3 pages.

*Primary Examiner* — Ling Choi
*Assistant Examiner* — Lanee Reuther
(74) *Attorney, Agent, or Firm* — James F. McBride; Steven W. Miller

(57) ABSTRACT

The present application relates to perfume compositions, delivery systems comprising such perfumes products comprising such perfumes and/or delivery systems, and processes for making and using same. Such perfumes and delivery systems provide improved perfume performance under high soil conditions and in cold water washing and a shell that at least partially surrounds said core.

1 Claim, No Drawings

(56) References Cited

U.S. PATENT DOCUMENTS

| | | |
|---|---|---|
| 2003/0216488 A1 | 11/2003 | Uchiyama et al. |
| 2004/0058845 A1 | 3/2004 | Metrot et al. |
| 2004/0071742 A1 | 4/2004 | Popplewell et al. |
| 2004/0071746 A1 | 4/2004 | Popplewell et al. |
| 2004/0072719 A1 | 4/2004 | Bennett et al. |
| 2004/0072720 A1 | 4/2004 | Brain et al. |
| 2004/0087476 A1 | 5/2004 | Dykstra et al. |
| 2004/0087477 A1 | 5/2004 | Ness |
| 2004/0091445 A1 | 5/2004 | Dykstra et al. |
| 2004/0092414 A1 | 5/2004 | Clapp et al. |
| 2004/0092425 A1 | 5/2004 | Boutique et al. |
| 2004/0106536 A1 | 6/2004 | Mane et al. |
| 2004/0110648 A1 | 6/2004 | Jordan et al. |
| 2005/0003980 A1 | 1/2005 | Baker et al. |
| 2005/0124530 A1 | 6/2005 | Creutz et al. |
| 2005/0130864 A1 | 6/2005 | Ouwendijk-Vrijenhoek et al. |
| 2005/0143282 A1 | 6/2005 | Creutz et al. |
| 2005/0276831 A1 | 12/2005 | Dihora et al. |
| 2006/0003913 A1 | 1/2006 | Boutique et al. |
| 2006/0039934 A1 | 2/2006 | Ness et al. |
| 2006/0263313 A1 | 11/2006 | Scavone et al. |
| 2006/0270587 A1 | 11/2006 | Shoji et al. |
| 2007/0020263 A1 | 1/2007 | Shitara et al. |
| 2007/0207942 A1 | 9/2007 | Creutz et al. |
| 2007/0275866 A1 | 11/2007 | Dykstra |

* cited by examiner

ENCAPSULATES

CROSS-REFERENCE TO RELATED APPLICATIONS

This application claims priority under 35 U.S.C. §119(e) to U.S. Provisional Application No. 61/287,795, filed Dec. 18, 2009.

FIELD OF INVENTION

The present application relates to perfume compositions, delivery systems comprising such perfumes products comprising such perfumes and/or delivery systems, and processes for making and using same.

BACKGROUND OF THE INVENTION

It is well known that detergent perfumes are less effective in washing conditions where the level of soil is high—for examples in warmer countries where levels of soil, for example, body soil, accumulation on fabrics are higher, or in geographies where wash water is recycled for reuse or where the wash process may be less efficient e.g handwash versus machine washing—or where the washing temperature is low—due to decreased performance of traditional laundry detergents in cold water. Without wishing to be limited by theory, it is believed that perfume materials, the majority of which are relatively hydrophobic, are attracted to high levels of hydrophobic soil in such wash solutions, rendering them more likely to be washed away with the soiled water (and therefore wasted). Moreover, in high soil conditions or in cold water the removal of the soil from fabrics is less effective, and soil residues can be left on the fabrics. The inventors have found that specific combinations of perfume raw materials (PRM's) provide superior odour masking/reduction of fabric odour even—when soil is left on the fabrics after washing. A potential draw back with such perfume compositions is that materials used in such compositions can have an undesired harsh, odour when used, neat, at high levels or when high residual levels of such materials are present on a situs, for example, damp fabrics. Thus, the inventors recognized that employing such perfumes via a perfume delivery system, for example, encapsulating such perfume compositions as described herein, further improves perfume performance under high soil conditions as the encapsulation decreases the interaction of the perfume raw materials with the soil and the appropriate level of perfume is applied to a situs as too much is not washed away with the soil nor do excessive levels of residual perfume materials build up on such sites.

SUMMARY OF THE INVENTION

The present application relates to perfume compositions, delivery systems comprising such perfumes products comprising such perfumes and/or delivery systems, and processes for making and using same.

DETAILED DESCRIPTION OF THE INVENTION

Definitions

As used herein "consumer product" means baby care, beauty care, fabric & home care, family care, feminine care, health care, or devices intended to be used or consumed in the form in which it is sold, and not intended for subsequent commercial manufacture or modification. Such products include but are not limited to diapers, bibs, wipes; products for and/or methods relating to treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use; and shaving products, products for and/or methods relating to treating fabrics, hard surfaces and any other surfaces in the area of fabric and home care, including: air care, car care, dishwashing, fabric conditioning (including softening), laundry detergency, laundry and rinse additive and/or care, hard surface cleaning and/or treatment, and other cleaning for consumer or institutional use; products and/or methods relating to bath tissue, facial tissue, paper handkerchiefs, and/or paper towels; tampons, and feminine napkins.

As used herein, the term "cleaning and/or treatment composition" includes, unless otherwise indicated, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, car or carpet shampoos, bathroom cleaners; hair shampoos and hair-rinses; shower gels and foam baths and metal cleaners; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists.

As used herein, the term "fabric care composition" includes, unless otherwise indicated, fabric softening compositions, fabric enhancing compositions, fabric freshening compositions and combinations there of.

As used herein, the articles "a" and "an" when used in a claim, are understood to mean one or more of what is claimed or described.

As used herein, the terms "include", "includes" and "including" are meant to be synonymous with the phrase "including but not limited to".

As used herein, the term "solid" includes granular, powder, bar and tablet product forms.

As used herein, the term "situs" includes paper products, fabrics, garments, hard surfaces, hair and skin.

The test methods disclosed in the Test Methods Section of the present application should be used to determine the respective values of the parameters of Applicants' inventions.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Perfume

In one aspect, a perfume that may comprise:
a) from about 3% to about 20% of a perfume raw material selected from the group of Table 1 perfume raw materials 85-88, 100, 108 and mixtures thereof;
b) from about 2% to about 35% of a perfume raw material selected from the group of Table 1 perfume raw materials 62-84, 114, 115 and mixtures thereof;
c) from about 2% to about 35% of a perfume raw material selected from the group of Table 1 perfume raw materials 1-61, 101, 102, 104, 109, 113 and mixtures thereof;
d) from about 0% to about 10% of a perfume raw material selected from the group of Table 1 perfume raw materials 99, 106, 111, 112 and mixtures thereof;
e) from about 0% to about 10% of a perfume raw material selected from the group of Table 1 perfume raw materials 89-94, 107, 110 and mixtures thereof; and
f) from about 0% to about 0.5% of a perfume raw material selected from the group of Table 1 perfume raw materials 95-98, 103, 105 and mixtures thereof
is disclosed.

In another aspect, a perfume that may comprise:
a) from about 3% to about 10% of a perfume raw material selected from the group of Table 1 perfume raw materials 85-88, 100, 108 and mixtures thereof;
b) from about 5% to about 10% of a perfume raw material selected from the group of Table 1 perfume raw materials 62-84, 114, 115 and mixtures thereof;
c) from about 5% to about 10% of a perfume raw material selected from the group of Table 1 perfume raw materials 1-61, 101, 102, 104, 109, 113 and mixtures thereof;
d) from about 2% to about 8% of a perfume raw material selected from the group of Table 1 perfume raw materials 99, 106, 111, 112 and mixtures thereof;
e) even from about 2% to about 8% of a perfume raw material selected from the group of Table 1 perfume raw materials 89-94, 107, 110 and mixtures thereof; and
f) from about 0% to about 0.5% of a perfume raw material selected from the group of Table 1 perfume raw materials 95-98, 103, 105 and mixtures thereof
is disclosed.

In another aspect, a perfume that may comprise:
a) from about 3% to about 7% of a perfume raw material selected from the group of Table 1 perfume raw materials 85-88, 100, 108 and mixtures thereof;
b) from about 2.5% to about 8% of a perfume raw material selected from the group of Table 1 perfume raw materials 62-84, 114, 115 and mixtures thereof;
c) from about 5% esters to about 8% of a perfume raw material selected from the group of Table 1 perfume raw materials 1-61, 101, 102, 104, 109, 113 and mixtures thereof;
d) 2% to about 8% of a perfume raw material selected from the group of Table 1 perfume raw materials 99, 106, 111, 112 and mixtures thereof;
e) 2% to about 8% of a perfume raw material selected from the group of Table 1 perfume raw materials 89-94, 107, 110 and mixtures thereof; and
f) from about 0% to about 0.5% of a perfume raw material selected from the group of Table 1 perfume raw materials 95-98, 103, 105 and mixtures thereof
is disclosed.

In another aspect, a perfume that may comprise:
a) from about 3% to about 20%, from about 3% to about 10%, or even from about 3% to about 7% of a perfume raw material selected from the group of Table 1 perfume raw materials 87, 100, 108 and mixtures thereof;
b) from about 2% to about 35% of a perfume raw material selected from the group of Table 1 perfume raw materials 62-64, 66, 76, 114, 115 and mixtures thereof;
c) from about 2% to about 35% of a perfume raw material selected from the group of Table 1 perfume raw materials 2-4, 11, 49, 91 and mixtures thereof;
d) from about 0% to about 10% of a perfume raw material selected from the group of Table 1 perfume raw materials 99, 106, 111, 112 and mixtures thereof;
e) from about 0% to about 10% of a perfume raw material selected from the group of Table 1 perfume raw materials 89-94, 107, 110 and mixtures thereof; and
f) from about 0% to about 0.5% of a perfume raw material selected from the group of Table 1 perfume raw materials 95-98, 103, 105 and mixtures thereof
is disclosed.

In another aspect, a perfume that may comprise:
a) from about 3% to about 20% of a perfume raw material selected from the group of Table 1 perfume raw materials 87, 100, 108 and mixtures thereof;
b) from about 2% to about 35% of a perfume raw material selected from the group of Table 1 perfume raw materials 114, 115 and mixtures thereof;
c) from about 2% to about 35% of a perfume raw material selected from the group of Table 1 perfume raw materials 2-4, 11, 49, 91 and mixtures thereof;
d) from about 0% to about 10% of a perfume raw material selected from the group of Table 1 perfume raw materials 99, 106, 111, 112 and mixtures thereof;
e) from about 0% to about 10% of a perfume raw material selected from the group of Table 1 perfume raw materials 89-94, 107, 110 and mixtures thereof; and
f) from about 0% to about 0.5% of a perfume raw material selected from the group of Table 1 perfume raw materials 95-98, 103, 105 and mixtures thereof
is disclosed.

Suitable Perfume Raw Materials

Perfumes that provide improved perfume performance under high soil conditions and in cold water may comprise Perfume Raw Materials as given in Table 1 below.

TABLE 1

Useful Perfume Raw Materials

| Item | Common Name | IUPAC Name |
|---|---|---|
| 1 | Methyl 2-methyl butyrate | methyl 2-methylbutanoate |
| 2 | Isopropyl 2-methyl butyrate | propan-2-yl 2-methylbutanoate |
| 3 | Ethyl-2 Methyl Butyrate | ethyl 2-methylbutanoate |
| 4 | Ethyl-2 Methyl Pentanoate | ethyl 2-methylpentanoate |
| 5 | Ethyl heptanoate | ethyl heptanoate |
| 6 | Ethyl octanoate | Ethyl octanoate |

TABLE 1-continued

Useful Perfume Raw Materials

| Item | Common Name | IUPAC Name |
|---|---|---|
| 7 | isobutyl hexanoate | 2-methylpropyl hexanoate |
| 8 | Amyl butyrate | pentyl butanoate |
| 9 | Amyl heptanoate | Pentyl heptanoate |
| 10 | Isoamyl isobutyrate | 3-methylbutyl 2-methylpropanoate |
| 11 | Hexyl acetate | hexyl acetate |
| 12 | hexyl butyrate | hexyl butanoate |
| 13 | hexyl isobutyrate | hexyl 2-methylpropanoate |
| 14 | hexyl isovalerate | hexyl 3-methylbutanoate |
| 15 | hexyl propionate | hexyl propanoate |
| 16 | Ethyl 2-cyclohexyl propanoate | ethyl 2-cyclohexylpropanoate |
| 17 | Ethyl 3,5,5-trimethyl hexanoate | ethyl 3,5,5-trimethylhexanoate |
| 18 | glyceryl 5-hydroxydecanoate | 2,3-dihydroxypropyl 5-hydroxydecanoate |
| 19 | Prenyl acetate | 3-methyl 2-butenyl acetate |
| 20 | 3-methyl 2-butenyl acetate | 3-methyl 2-butenyl acetate |
| 21 | methyl 3-nonenoate | methyl non-3-enoate |
| 22 | Ethyl (E)-dec-4-enoate | Ethyl (E)-dec-4-enoate |
| 23 | Ethyl (E)-oct-2-enoate | Ethyl (E)-oct-2-enoate |
| 24 | Ethyl 2,4-decadienoate | ethyl (2E,4Z)-deca-2,4-dienoate |
| 25 | Ethyl 3-octenoate | ethyl (E)-oct-3-enoate |
| 26 | Citronellyl acetate | 3,7-dimethyloct-6-enyl acetate |
| 27 | Ethyl trans-2-decenoate | ethyl (E)-dec-2-enoate |
| 28 | 2-hexen-1-yl isovalerate | [(E)-hex-2-enyl] acetate |
| 29 | 2-hexen-1-yl propionate | [(E)-hex-2-enyl] propanoate |
| 30 | 2-hexen-1-yl valerate | [(E)-hex-2-enyl] pentanoate |
| 31 | 3-hexen-1-yl (E)-2-hexenoate | [(Z)-hex-3-enyl] (E)-hex-2-enoate |
| 32 | 3-Hexen-1-yl 2-methyl butyrate | [(Z)-hex-3-enyl] 2-methylbutanoate |
| 33 | 3-hexen-1-yl acetate | [(Z)-hex-3-enyl] acetate |
| 34 | 3-hexen-1-yl benzoate | [(Z)-hex-3-enyl] benzoate |
| 35 | 3-hexen-1-yl formate | [(Z)-hex-3-enyl] formate |
| 36 | 3-hexen-1-yl tiglate | [(Z)-hex-3-enyl] (Z)-2-methylbut-2-enoate |
| 37 | 2-methyl butyl 2-methyl butyrate | 2-methylbutyl 2-methylbutanoate |
| 38 | Butyl isovalerate | butyl 3-methylbutanoate |
| 39 | Geranyl acetate | [(2E)-3,7-dimethylocta-2,6-dienyl] acetate |
| 40 | Geranyl butyrate | [(2E)-3,7-dimethylocta-2,6-dienyl] butanoate |
| 41 | Geranyl isovalerate | [(3E)-3,7-dimethylocta-3,6-dienyl] 3-methylbutanoate |
| 42 | Geranyl propionate | [(2E)-3,7-dimethylocta-2,6-dienyl] propanoate |
| 43 | Allyl cyclohexane acetate | prop-2-enyl 2-cyclohexylacetate |
| 44 | Allyl Cyclohexyl Propionate | prop-2-enyl 3-cyclohexylpropanoate |
| 45 | allyl cyclohexyl valerate | prop-2-enyl 5-cyclohexylpentanoate |
| 46 | benzyl octanoate | benzyl octanoate |
| 47 | cocolactone | 6-pentyl-5,6-dihydropyran-2-one |
| 48 | coconut decanone | 8-methyl-1-oxaspiro(4.5)decan-2-one |
| 49 | gamma undecalactone | 5-heptyloxolan-2-one |
| 50 | gamma-decalactone | 5-hexyloxolan-2-one |
| 51 | gamma-dodecalactone | 5-octyloxolan-2-one |
| 52 | jasmin lactone | 6-[(E)-pent-2-enyl]oxan-2-one |
| 53 | Jasmolactone | 5-[(Z)-hex-3-enyl]oxolan-2-one |
| 54 | Nonalactone | 6-butyloxan-2-one |
| 55 | 6-acetoxydihydrotheaspirane | [2a,5a(S*)]-2,6,10,10-tetramethyl-1-oxaspiro[4.5]decan-6-yl acetate |
| 56 | Phenoxyethyl isobutyrate | 2-(phenoxy)ethyl 2-methylpropanoate |
| 57 | Pivacyclene | |
| 58 | Verdox | (2-tert-butylcyclohexyl) acetate |
| 59 | cyclobutanate | 3a,4,5,6,7,7a-hexahydro-4,7-methano-1g-inden-5(or 6)-yl butyrate |
| 60 | Dimethyl Anthranilate | methyl 2-methylaminobenzoate |
| 61 | Methyl Antranilate | methyl 2-aminobenzoate |
| 62 | Octyl Aldehyde | Octanal |
| 63 | Nonanal | Nonanal |
| 64 | Decyl aldehyde | Decanal |
| 65 | Lauric Aldehyde | Dodecanal |
| 66 | Methyl Nonyl Acetaldehyde | 2-methyl undecanal |
| 67 | Methyl Octyl Acetaldehyde | 2-methyl decanal |
| 68 | 2,4-Hexadienal | (2E,4E)-hexa-2,4-dienal |
| 69 | Intreleven Aldehyde | undec-10-enal |
| 70 | Decen-1-al | (E)-dec-2-enal |
| 71 | Nonen-1-al | (E)-2-nonen-1-al |
| 72 | Adoxal | 2,6,10-trimethylundec-9-enal |
| 73 | Geraldehyde | (4Z)-5,9-dimethyldeca-4,8-dienal |
| 74 | Iso cyclo citral | 2,4,6-trimethylcyclohex-3-ene-1-carbaldehyde |
| 75 | d-limonene mainly | 1-methyl-4-prop-1-en-2-yl-cyclohexene |
| 76 | Ligustral | 2,4-dimethylcyclohex-3-ene-1-carbaldehyde |
| 77 | Myrac aldehyde | 4-(4-methylpent-3-enyl)cyclohex-3-ene-1-carbaldehyde |
| 78 | Tridecenal | tridec-2-enal |
| 79 | Triplal | 2,4-dimethyl-3-cyclohexene-1-carboxaldehyde |
| 80 | Vertoliff | 1,2-dimethylcyclohex-3-ene-1-carbaldehyde |

TABLE 1-continued

Useful Perfume Raw Materials

| Item | Common Name | IUPAC Name |
|---|---|---|
| 81 | Cyclal C | 2,4-dimethylcyclohex-3-ene-1-carbaldehyde |
| 82 | Anisic aldehyde | 4-methoxybenzaldehyde |
| 83 | Helional | 3-(1,3-benzodioxol-5-yl)-2-methylpropanal |
| 84 | Heliotropin | 1,3-benzodioxole-5-carbaldehyde |
| 85 | Neocaspirene | |
| 86 | Beta Naphthol Ethyl Ether | 2-ethoxynaphtalene |
| 87 | Beta Naphthol Methyl Ether | 2-methoxynaphtalene |
| 88 | hyacinth ether | 2-cyclohexyloxyethylbenzene |
| 89 | 2-heptyl cyclopentanone (fleuramone) | 2-heptylcyclopentan-1-one |
| 90 | menthone-8-thioacetate | O-[2-[(1S)-4-methyl-2-oxocyclohexyl]propan-2-yl] ethanethioate |
| 91 | Nectaryl | 2-[2-(4-methyl-1-cyclohex-3-enyl)propyl]cyclopentan-1-one |
| 92 | Phenyl Naphthyl Ketone | naphthalen-2-yl-phenylmethanone |
| 93 | decen-1-yl cyclopentanone | 2-[(2E)-3,7-dimethylocta-2,6-dienyl]cyclopentan-1-one |
| 94 | fruity cyclopentanone (veloutone) | 2,2,5-trimethyl-5-pentylcyclopentan-1-one |
| 95 | 4-methoxy-2-methyl butane thiol (blackcurrant mercaptan) | 4-methoxy-2-methylbutane-2-thiol |
| 96 | Grapefruit Mercaptan | 2-(4-methyl-1-cyclohex-3-enyl)propane-2-thiol |
| 97 | Buccoxime | N-(1,5-dimethyl-8-bicyclo [3.2.1] octanylidene)hydroxylamine |
| 98 | Labienoxime | 2,4,4,7-Tetramethyl-6,8-nonadiene-3-one oxime |
| 99 | Undecavertol | (E)-4-methyldec-3-en-5-ol |
| 100 | Decanal diethyl acetal | 1,1-diethoxydecane |
| 101 | Diethyl maleate | diethyl but-2-enedioate |
| 102 | Ethyl Acetoacetate | ethyl 3-oxobutanoate |
| 103 | frutonile | 2-Methyldecanenitrile |
| 104 | Methyl dioxolan | ethyl 2-(2-methyl-1,3-dioxolan-2-yl)acetate |
| 105 | Cetalox | 3a,6,6,9a-tetramethyl-2,4,5,5a,7,8,9,9b-octahydro-1H-benzo[e][1]benzofuran |
| 106 | Cyclopentol | |
| 107 | Delta-damascone | (E)-1-(2,6,6-trimethyl-1-cyclohex-3-enyl)but-2-en-1-one |
| 108 | Eucalyptol | 1,3,3-trimethyl-2-oxabicyclo[2,2,2]octane |
| 109 | Flor acetate | |
| 110 | Ionone gamma methyl | (E)-3-methyl-4-(2,6,6-trimethyl-1-cyclohex-2-enyl)but-3-en-2-one |
| 111 | Laevo trisandol | |
| 112 | Linalool | 3,7-dimethylocta-1,6-dien-3-ol |
| 113 | Violiff | [(4Z)-1-cyclooct-4-enyl] methyl carbonate |
| 114 | Cymal | 3-(4-propan-2-ylphenyl)butanal |
| 115 | Bourgeonal | 3-(4-tert-butylphenyl)propanal |

Perfume Delivery Systems

As disclosed, the benefits of the perfumes disclosed herein may be further enhanced by employing a perfume delivery system to apply such perfumes. Non-limiting examples of suitable perfume delivery systems, methods of making perfume delivery systems and the uses of such perfume delivery systems are disclosed in USPA 2007/0275866 A1. Such perfume delivery systems include:

Polymer Assisted Delivery (PAD): This perfume delivery technology uses polymeric materials to deliver perfume materials. Classical coacervation, water soluble or partly soluble to insoluble charged or neutral polymers, liquid crystals, hot melts, hydrogels, perfumed plastics, microcapsules, nano- and micro-latexes, polymeric film formers, and polymeric absorbents, polymeric adsorbents, etc. are some examples. PAD includes but is not limited to:

Matrix Systems The fragrance is dissolved or dispersed in a polymer matrix or particle. Perfumes, for example, may be 1) dispersed into the polymer prior to formulating into the product or 2) added separately from the polymer during or after formulation of the product. Diffusion of perfume from the polymer is a common trigger that allows or increases the rate of perfume release from a polymeric matrix system that is deposited or applied to the desired surface (situs), although many other triggers are know that may control perfume release. Absorption and/or adsorption into or onto polymeric particles, films, solutions, and the like are aspects of this technology. Nano- or micro-particles composed of organic materials (e.g., latexes) are examples. Suitable particles include a wide range of materials including, but not limited to polyacetal, polyacrylate, polyacrylic, polyacrylonitrile, polyamide, polyaryletherketone, polybutadiene, polybutylene, polybutylene terephthalate, polychloroprene, poly ethylene, polyethylene terephthalate, polycyclohexylene dimethylene terephthalate, polycarbonate, polychloroprene, polyhydroxyalkanoate, polyketone, polyester, polyethylene, polyetherimide, polyethersulfone, polyethylenechlorinates, polyimide, polyisoprene, polylactic acid, polymethylpentene, polyphenylene oxide, polyphenylene sulfide, polyphthalamide, polypropylene, polystyrene, polysulfone, polyvinyl acetate, polyvinyl chloride, as well as polymers or copolymers based on acrylonitrile-butadiene, cellulose acetate, ethylene-vinyl acetate, ethylene vinyl alcohol, styrene-butadiene, vinyl acetate-ethylene, and mixtures thereof.

"Standard" systems refer to those that are "pre-loaded" with the intent of keeping the pre-loaded perfume associated with the polymer until the moment or moments of perfume release. Such polymers may also suppress the neat product odor and provide a bloom and/or longevity benefit depending on the rate of perfume release. One challenge with such systems is to achieve the ideal balance between 1) in-product stability (keeping perfume inside carrier until you need it) and 2) timely release (during use or from dry situs). Achieving such stability is particularly important during in-product storage and product aging. This challenge is particularly apparent for aqueous-based, surfactant-containing products, such as heavy duty liquid laundry detergents. Many "Standard" matrix systems available effectively become "Equilibrium" systems when formulated into aqueous-based products. One may select an "Equilibrium" system or a Reservoir system, which has acceptable in-product diffusion stability and available triggers for release (e.g., friction). "Equilibrium" systems are those in which the perfume and polymer may be added separately to the product, and the equilibrium interaction between perfume and polymer leads to a benefit at one or more consumer touch points (versus a free perfume control that has no polymer-assisted delivery technology). The polymer may also be pre-loaded with perfume; however, part or all of the perfume may diffuse during in-product storage reaching an equilibrium that includes having desired perfume raw materials (PRMs) associated with the polymer. The polymer then carries the perfume to the surface, and release is typically via perfume diffusion. The use of such equilibrium system polymers has the potential to decrease the neat product odor intensity of the neat product (usually more so in the case of pre-loaded standard system). Deposition of such polymers may serve to "flatten" the release profile and provide increased longevity. As indicated above, such longevity would be achieved by suppressing the initial intensity and may enable the formulator to use more high impact or low odor detection threshold (ODT) or low Kovats Index (KI) PRMs to achieve FMOT benefits without initial intensity that is too strong or distorted. It is important that perfume release occurs within the time frame of the application to impact the desired consumer touch point or touch points. Suitable micro-particles and micro-latexes as well as methods of making same may be found in USPA 2005/0003980 A1. Matrix systems also include hot melt adhesives and perfume plastics. In addition, hydrophobically modified polysaccharides may be formulated into the perfumed product to increase perfume deposition and/or modify perfume release. All such matrix systems, including for example polysaccarides and nanolatexes may be combined with other PDTs, including other PAD systems such as PAD reservoir systems in the form of a perfume microcapsule (PMC). Polymer Assisted Delivery (PAD) matrix systems may include those described in the following references: US Patent Applications 2004/0110648 A1; 2004/0092414 A1; 2004/0091445 A1 and 2004/0087476 A1; and U.S. Pat. Nos. 6,531,444; 6,024,943; 6,042,792; 6,051,540; 4,540,721 and 4,973,422.

Silicones are also examples of polymers that may be used as PDT, and can provide perfume benefits in a manner similar to the polymer-assisted delivery "matrix system". Such a PDT is referred to as silicone-assisted delivery (SAD). One may pre-load silicones with perfume, or use them as an equilibrium system as described for PAD. Suitable silicones as well as making same may be found in WO 2005/102261; USPA 20050124530A1; USPA 20050143282A1; and WO 2003/015736. Functionalized silicones may also be used as described in USPA 2006/003913 A1. Examples of silicones include polydimethylsiloxane and polyalkyldimethylsiloxanes. Other examples include those with amine functionality, which may be used to provide benefits associated with amine-assisted delivery (AAD) and/or polymer-assisted delivery (PAD) and/or amine-reaction products (ARP). Other such examples may be found in U.S. Pat. No. 4,911,852; USPA 2004/0058845 A1; USPA 2004/0092425 A1 and USPA 2005/0003980 A1.

Reservoir Systems: Reservoir systems are also known as a core-shell type technology, or one in which the fragrance is surrounded by a perfume release controlling membrane, which may serve as a protective shell. The material inside the microcapsule is referred to as the core, internal phase, or fill, whereas the wall is sometimes called a shell, coating, or membrane. Microparticles or pressure sensitive capsules or microcapsules are examples of this technology. Microcapsules of the current invention are formed by a variety of procedures that include, but are not limited to, coating, extrusion, spray-drying, interfacial, in-situ and matrix polymerization. The possible shell materials vary widely in their stability toward water. Among the most stable are polyoxymethyleneurea (PMU)-based materials, which may hold certain PRMs for even long periods of time in aqueous solution (or product). Such systems include but are not limited to urea-formaldehyde and/or melamine-formaldehyde. Gelatin-based microcapsules may be prepared so that they dissolve quickly or slowly in water, depending for example on the degree of cross-linking. Many other capsule wall materials are available and vary in the degree of perfume diffusion stability observed. Without wishing to be bound by theory, the rate of release of perfume from a capsule, for example, once deposited on a surface is typically in reverse order of in-product perfume diffusion stability. As such, urea-formaldehyde and melamine-formaldehyde microcapsules for example, typically require a release mechanism other than, or in addition to, diffusion for release, such as mechanical force (e.g., friction, pressure, shear stress) that serves to break the capsule and increase the rate of perfume (fragrance) release. Other triggers include melting, dissolution, hydrolysis or other chemical reaction, electromagnetic radiation, and the like. The use of pre-loaded microcapsules requires the proper ratio of in-product stability and in-use and/or on-surface (on-situs) release, as well as proper selection of PRMs. Microcapsules that are based on urea-formaldehyde and/or melamine-formaldehyde are relatively stable, especially in near neutral aqueous-based solutions. These materials may require a friction trigger which may not be applicable to all product applications. Other microcapsule materials (e.g., gelatin) may be unstable in aqueous-based products and may even provide reduced benefit (versus free perfume control) when in-product aged. Scratch and sniff technologies are yet another example of PAD. Perfume microcapsules (PMC) may include those described in the following references: US Patent Applications: 2003/0125222 A1; 2003/215417 A1; 2003/216488 A1; 2003/158344 A1; 2003/165692 A1; 2004/071742 A1; 2004/071746 A1; 2004/072719 A1; 2004/072720 A1; 2006/0039934 A1; 2003/203829 A1; 2003/195133 A1; 2004/087477 A1; 2004/0106536 A1; and U.S. Pat. Nos. 6,645,479 B1; 6,200,949 B1; 4,882,220; 4,917,920; 4,514,461; 6,106,875 and 4,234,627, 3,594,328 and US RE 32713.

Molecule-Assisted Delivery (MAD): Non-polymer materials or molecules may also serve to improve the delivery of perfume. Without wishing to be bound by theory, perfume may non-covalently interact with organic materials, resulting in altered deposition and/or release. Non-limiting examples of such organic materials include but are not limited to hydrophobic materials such as organic oils, waxes, mineral oils, petrolatum, fatty acids or esters, sugars, surfactants, liposomes and even other perfume raw material (perfume oils), as well as natural oils, including body and/or other soils. Perfume fixatives are yet another example. In one aspect, non-polymeric materials or molecules have a CLogP greater than about 2. Molecule-Assisted Delivery (MAD) may also include those described in U.S. Pat. No. 7,119,060 and U.S. Pat. No. 5,506,201.

Cyclodextrin (CD): This technology approach uses a cyclic oligosaccharide or cyclodextrin to improve the delivery of perfume. Typically a perfume and cyclodextrin (CD) complex is formed. Such complexes may be preformed, formed in-situ, or formed on or in the situs. Without wishing to be bound by theory, loss of water may serve to shift the equilibrium toward the CD-Perfume complex, especially if other adjunct ingredients (e.g., surfactant) are not present at high concentration to compete with the perfume for the cyclodextrin cavity. A bloom benefit may be achieved if water exposure or an increase in moisture content occurs at a later time point. In addition, cyclodextrin allows the perfume formulator increased flexibility in selection of PRMs. Cyclodextrin may be pre-loaded with perfume or added separately from perfume to obtain the desired perfume stability, deposition or release benefit. Suitable CDs as well as methods of making same may be found in USPA 2005/0003980 A1 and 2006/0263313 A1 and U.S. Pat. Nos. 5,552,378; 3,812,011; 4,317,881; 4,418,144 and 4,378,923.

Starch Encapsulated Accord (SEA): The use of a starch encapsulated accord (SEA) technology allows one to modify the properties of the perfume, for example, by converting a liquid perfume into a solid by adding ingredients such as starch. The benefit includes increased perfume retention during product storage, especially under non-aqueous conditions. Upon exposure to moisture, a perfume bloom may be triggered. Benefits at other moments of truth may also be achieved because the starch allows the product formulator to select PRMs or PRM concentrations that normally cannot be used without the presence of SEA. Another technology example includes the use of other organic and inorganic materials, such as silica to convert perfume from liquid to solid. Suitable SEAs as well as methods of making same may be found in USPA 2005/0003980 A1 and U.S. Pat. No. 6,458,754 B1.

Zeolite & Inorganic Carrier (ZIC): This technology relates to the use of porous zeolites or other inorganic materials to deliver perfumes. Perfume-loaded zeolite may be used with or without adjunct ingredients used for example to coat the perfume-loaded zeolite (PLZ) to change its perfume release properties during product storage or during use or from the dry situs. Suitable zeolite and inorganic carriers as well as methods of making same may be found in USPA 2005/0003980 A1 and U.S. Pat. Nos. 5,858,959; 6,245,732 B1; 6,048,830 and 4,539,135. Silica is another form of ZIC. Another example of a suitable inorganic carrier includes inorganic tubules, where the perfume or other active material is contained within the lumen of the nano- or micro-tubules. Preferably, the perfume-loaded inorganic tubule (or Perfume-Loaded Tubule or PLT) is a mineral nano- or micro-tubule, such as halloysite or mixtures of halloysite with other inorganic materials, including other clays. The PLT technology may also comprise additional ingredients on the inside and/or outside of the tubule for the purpose of improving in-product diffusion stability, deposition on the desired situs or for controlling the release rate of the loaded perfume. Monomeric and/or polymeric materials, including starch encapsulation, may be used to coat, plug, cap, or otherwise encapsulate the PLT. Suitable PLT systems as well as methods of making same may be found in U.S. Pat. No. 5,651,976.

In one aspect, a perfume delivery system selected from the group consisting of a Polymer Assisted Delivery (PAD) system, Molecule-Assisted Delivery (MAD) system, Cyclodextrin (CD) system, Starch Encapsulated Accord (SEA) system, Zeolite & Inorganic Carrier (ZIC) system, wherein said perfume delivery system may comprise a perfume disclosed in this specification, for example a perfume selected from the perfumes disclosed in the perfume section of this specification, is disclosed.

In one aspect, a Polymer Assisted Delivery (PAD) system wherein said Polymer Assisted Delivery (PAD) system may comprise a Polymer Assisted Delivery (PAD) Reservoir system that may comprise a perfume disclosed in this specification, for example a perfume selected from the perfumes disclosed in the perfume section of this specification, is disclosed.

In one aspect of, said Polymer Assisted Delivery (PAD) Reservoir system said Polymer Assisted Delivery (PAD) Reservoir system may comprise a perfume delivery particle that may comprise a shell material and a core material, said shell material encapsulating said core material, said core material may comprise a perfume disclosed in this specification, for example a perfume selected from the perfumes disclosed in the perfume section of this specification, and said shell comprising a material selected from the group consisting of polyethylenes; polyamides; polystyrenes; polyisoprenes; polycarbonates; polyesters; polyacrylates; aminoplasts, in one aspect said aminoplast comprises a polyureas, polyurethane, and/or polyureaurethane, in one aspect said polyurea comprises polyoxymethyleneurea and/or melamine formaldehyde; polyolefins; polysaccharides, in one aspect alginate and/or chitosan; gelatin; shellac; epoxy resins; vinyl polymers; water insoluble inorganics; silicone; and mixtures thereof.

In one aspect, of said Polymer Assisted Delivery (PAD) Reservoir system said shell may comprise melamine formaldehyde and/or cross linked melamine formaldehyde.

In one aspect of said Polymer Assisted Delivery (PAD) Reservoir system said shell may be coated by a water-soluble cationic polymer selected from the group that consists of polysaccharides, cationically modified starch and cationically modified guar, polysiloxanes, dimethyldiallylammonium polyhalogenides, copolymers of dimethyldiallylammonium polychloride and vinyl pyrrolidone, acrylamides, imidazoles, imidazolinium halogenides and imidazolium halogenides and polyvinyl amine and its copolymers with N-vinyl formamide.

In one aspect of said Polymer Assisted Delivery (PAD) Reservoir system said coating that coats said shell, may comprise a cationic polymer and an anionic polymer.

In one aspect of said Polymer Assisted Delivery (PAD) Reservoir system wherein said cationic polymer may comprise hydroxylethyl cellulose; and said anionic polymer may comprise carboxylmethyl cellulose.

In one aspect, said Polymer Assisted Delivery (PAD) Reservoir system is a perfume microcapsule.

Process of Making Encapsulates

In one aspect, a process that may comprise:
a.) preparing a first solution that may comprise, based on total solution weight from about 20% to about 90%, from about 40% to about 80%, or even from about 60% to about 80% water, of a first emulsifier and a first resin, the ratio of said first emulsifier and said first resin being from about 0.1:0 to about 10:0, from about 0.1:1 to about 10:1, from about 0.5:1 to about 3:1, or even from about 0.8:1 to about 1.1:1;

b.) preparing a second solution that may comprise based on total solution weight from about 20% to about 95% water, of a second emulsifier and a second resin, the ratio of said second emulsifier and said second resin being from about 0:1 to about 3:1, from about 0.04:1 to about 0.2:1, or even from about 0.05:1 to about 0.15:1;

c.) combining a core material that may comprise a perfume disclosed in the present specification and said first solution to form a first composition;

d.) emulsifying said first composition;

e.) combining said first composition and said second solution to form a second composition and optionally combining any processing aids and said second composition—said first composition and said second solution may be combined in any order but in one aspect said second solution is added to said first composition or said second solution and said first composition are combined simultaneously;

f.) mixing said second composition for at least 15 minutes, at least 1 hour or even from about 4 hours to about 100 hours at a temperature of from about 25° C. to about 100° C., from about 45° C. to about 90° C., or even from about 50° C. to about 80° C. heat and optionally combining any processing aids to said second composition;

g.) optionally combining any scavenger material, structurant, and/or anti-agglomeration agent with said second composition during step f.) or thereafter—such materials may be combined in any order but in one aspect the scavenger material is combined first, any structurant second, and then anti-agglomeration agent is combined; and h.) optionally spray drying said second composition is disclosed.

In one or more aspects of the process, said first and second resins may comprise the reaction product of an aldehyde and an amine, suitable aldehydes include, formaldehyde. Suitable amines include melamine, urea, benzoguanamine, glycoluril, and mixtures thereof. Suitable melamines include, methylol melamine, methylated methylol melamine, imino melamine and mixtures thereof. Suitable ureas include, dimethylol urea, methylated dimethylol urea, urea-resorcinol, and mixtures thereof.

In one or more aspects of the process, said first and second emulsifiers may comprise a moiety selected from the group consisting of carboxy, hydroxyl, thiol, amine, amide and combinations thereof. In one aspect, said emulsifier may have a pKa of less than 5, preferably greater than 0 but less than 5. Emulsifiers include acrylic acid-alkyl acrylate copolymer, poly(acrylic acid), polyoxyalkylene sorbitan fatty esters, polyalkylene co-carboxy anhydrides, polyalkylene co-maleic anhydrides, poly(methyl vinyl ether-co-maleic anhydride), poly(propylene-co-maleic anhydride), poly(butadiene co-maleic anhydride), and poly(vinyl acetate-co-maleic anhydride), polyvinyl alcohols, polyalkylene glycols, polyoxyalkylene glycols, and mixtures thereof.

In one or more aspects of the process, the pH of the first and second solutions may be controlled such that the pH of said first and second solution is from about 3.0 to 7.0.

In one or more aspects of the process, during step f.), from about 0% to about 10%, from about 1% to about 5% or even from about 2% to about 4%, based on total second composition weight, of a salt comprising an anion and cation, said anion being selected from the group consisting of chloride, sulfate, phosphate, nitrate, polyphosphate, citrate, maleate, fumarate and mixtures thereof; and said cation being selected from the group consisting of a Periodic Group IA element, Periodic Group IIA element, ammonium cation and mixtures thereof, preferably sodium sulfate, may be combined with said second composition.

In one or more aspects of the process, any of the aforementioned processing parameters may be combined.

Supplemental teachings of making suitable encapsulates as well as suitable shell materials are described in U.S. Pat. No. 6,869,923 B1 and US Published Patent Applications Nos. 2005/0276831 A1 and 2007/020263 A1. Suitable equipment for use in the processes disclosed herein may include continuous stirred tank reactors, homogenizers, turbine agitators, recirculating pumps, paddle mixers, ploughshear mixers, ribbon blenders, vertical axis granulators and drum mixers, both in batch and, where available, in continuous process configurations, spray dryers, and extruders. Such equipment can be obtained from Lodige GmbH (Paderborn, Germany), Littleford Day, Inc. (Florence, Ky., U.S.A.), Forberg AS (Larvik, Norway), Glatt Ingenieurtechnik GmbH (Weimar, Germany), Niro (Soeborg, Denmark), Hosokawa Bepex Corp. (Minneapolis, Minn., U.S.A.), Arde Barinco (New Jersey, U.S.A.).

Compositions

In one aspect, a composition that may comprise any aspect of the perfume delivery systems and/or perfumes disclosed in the present specification is disclosed.

In one aspect, said composition may be a consumer product.

In one aspect, such composition may be a consumer product that may comprise, based on total composition weight, from about 0.001% to about 50%, from about 0.01% to about 10%, or even from about 0.1% to about 5%, of a perfume disclosed in the present specification—from about 0.001% to about 90%, from about 0.01% to about 50%, or even from about 0.1% to about 10%, of said perfume, based on said perfume's weight, may be provided by a perfume delivery system according to the present specification.

In one aspect, said composition may comprise an encapsulate wherein said encapsulate's density may be such that the density ratio of said encapsulate to one or more fluids of the composition's fluids may be from about 0.9:1 to about 1.1:1; from about 0.98:1 to about 1.02:1; from about 0.99:1 to about 1.01:1 or even 1:1.

In one aspect, any of the aforementioned compositions may comprise a cleaning and/or treatment ingredient.

In one aspect, any of the aforementioned compositions' encapsulates may be a perfume microcapsule.

In one aspect, any of the aforementioned compositions may comprise one or more cleaning and/or treatment agents selected from the adjunct ingredients listed in the present specification.

While the precise level of encapsulate that is employed depends on the type and end use of the, consumer product, in one aspect a consumer product may comprise, based on total composition weight, at least about 0.01%, from about 0.01% to about 80%, or even from about 0.02% to about 10% wt % of a encapsulate disclosed herein.

In one aspect, a consumer product that is compact is disclosed.

In one aspect, a consumer products including liquid detergents having a water content, based on total consumer product formulation weight, of from about 0% to about 15%, from about 0.5% to about 10% or even from about 1% to about 8% water are disclosed.

In one aspect, the consumer product is a cleaning and/or treatment composition or fabric care composition that may comprise an encapsulate disclosed in the present specification and at least one cleaning and/or treatment composition or fabric care adjunct ingredient.

In one aspect, a cleaning composition may comprise, from about 0.005% to about 5% weight % of such encapsulate based on total cleaning composition weight of such encapsulate. In one aspect, a fabric treatment composition may comprise, based on total fabric treatment composition weight from about 0.005% to about 20% of such encapsulate.

Aspects of the invention include the use of the encapsulates of the present invention in detergent compositions (e.g., TIDE™), hard surface cleaners (e.g., MR CLEAN™), automatic dishwashing liquids (e.g., CASCADE™), dishwashing liquids (e.g., DAWN™), and floor cleaners (e.g., SWIFFER™). Non-limiting examples of cleaning compositions may include those described in U.S. Pat. Nos. 4,515,705; 4,537,706; 4,537,707; 4,550,862; 4,561,998; 4,597,898; 4,968,451; 5,565,145; 5,929,022; 6,294,514; 6,376,445; 7,169,741 B2 and 7,297,674 B2 as well as in U.S. Patent Application Publication No. 2005/0130864 A1. The cleaning compositions disclosed herein may be formulated such that, during use in aqueous cleaning operations, the wash water will have a pH of between about 6.5 and about 12, or between about 7.5 and 10.5. Liquid dishwashing product formulations typically have a pH between about 6.8 and about 9.0. Cleaning products are typically formulated to have a pH of from about 2 to about 11. Techniques for controlling pH at recommended usage levels include the use of buffers, alkalis, acids, etc., and are well known to those skilled in the art.

Fabric treatment compositions disclosed herein typically comprise a fabric softening active ("FSA"). Suitable fabric softening actives, include, but are not limited to, materials selected from the group consisting of quats, amines, fatty esters, sucrose esters, silicones, dispersible polyolefins, clays, polysaccharides, fatty oils, polymer latexes and mixtures thereof.

Formaldehyde Scavenger

In one aspect, the perfume delivery system disclosed herein may be combined with a formaldehyde scavenger. In one aspect, such perfume delivery system may comprise the encapsulates of the present invention. Suitable formaldehyde scavengers include materials selected from the group consisting of sodium bisulfite, melamine, urea, ethylene urea, cysteine, cysteamine, lysine, glycine, serine, carnosine, histidine, glutathione, 3,4-diaminobenzoic acid, allantoin, glycouril, anthranilic acid, methyl anthranilate, methyl 4-aminobenzoate, ethyl acetoacetate, acetoacetamide, malonamide, ascorbic acid, 1,3-dihydroxyacetone dimer, biuret, oxamide, benzoguanamine, pyroglutamic acid, pyrogallol, methyl gallate, ethyl gallate, propyl gallate, triethanol amine, succinamide, thiabendazole, benzotriazol, triazole, indoline, sulfanilic acid, oxamide, sorbitol, glucose, cellulose, poly (vinyl alcohol), partially hydrolyzed poly(vinylformamide), poly(vinyl amine), poly(ethylene imine), poly(oxyalkyleneamine), poly(vinyl alcohol)-co-poly(vinyl amine), poly(4-aminostyrene), poly(1-lysine), chitosan, hexane diol, ethylenediamine-N,N'-bisacetoacetamide, N-(2-ethylhexyl) acetoacetamide, 2-benzoylacetoacetamide, N-(3-phenylpropyl)acetoacetamide, lilial, helional, melonal, triplal, 5,5-dimethyl-1,3-cyclohexanedione, 2,4-dimethyl-3-cyclohexenecarboxaldehyde, 2,2-dimethyl-1,3-dioxan-4,6-dione, 2-pentanone, dibutyl amine, triethylenetetramine, ammonium hydroxide, benzylamine, hydroxycitronellol, cyclohexanone, 2-butanone, pentane dione, dehydroacetic acid, or a mixture thereof. These formaldehyde scavengers may be obtained from Sigma/Aldrich/Fluka of St. Louis, Mo. U.S.A. or PolySciences, Inc. of Warrington, Pa., U.S.A.

Such formaldehyde scavengers are typically combined with a slurry containing said benefit agent containing delivery particle, at a level, based on total slurry weight, of from about 2 wt. % to about 18 wt. %, from about 3.5 wt. % to about 14 wt. % or even from about 5 wt. % to about 13 wt. %.

In one aspect, such formaldehyde scavengers may be combined with a product containing a benefit agent containing delivery particle, said scavengers being combined with said product at a level, based on total product weight, of from about 0.005% to about 0.8%, alternatively from about 0.03% to about 0.5%, alternatively from about 0.065% to about 0.25% of the product formulation.

Adjunct Materials

While not essential for each consumer product embodiment of the present invention, the non-limiting list of adjuncts illustrated hereinafter are suitable for use in the instant consumer products and may be desirably incorporated in certain embodiments of the invention, for example to assist or enhance performance, for treatment of the substrate to be cleaned, or to modify the aesthetics of the composition as is the case with perfumes, colorants, dyes or the like. The precise nature of these additional components, and levels of incorporation thereof, will depend on the physical form of the composition and the nature of the operation for which it is to be used. Such adjunct are in addition to the perfumes and/or perfume delivery systems previously disclosed herein. Suitable adjunct materials include, but are not limited to, surfactants, builders, chelating agents, dye transfer inhibiting agents, dispersants, enzymes, and enzyme stabilizers, catalytic materials, bleach activators, polymeric dispersing agents, clay soil removal/anti-redeposition agents, brighteners, suds suppressors, dyes, additional perfume and perfume delivery systems, structure elasticizing agents, thickeners/structurants, fabric softeners, carriers, hydrotropes, processing aids and/or pigments. In addition to the disclosure below, suitable examples of such other adjuncts and levels of use are found in U.S. Pat. Nos. 5,576,282, 6,306,812 B1 and 6,326,348 B1 that are incorporated by reference.

As stated, the adjunct ingredients are not essential for each consumer product embodiment of the present invention. Thus, certain embodiments of Applicants' compositions do not contain one or more of the following adjuncts materials: bleach activators, surfactants, builders, chelating agents, dye transfer inhibiting agents, dispersants, enzymes, and enzyme stabilizers, catalytic metal complexes, polymeric dispersing agents, clay and soil removal/anti-redeposition agents, brighteners, suds suppressors, dyes, additional perfumes and perfume delivery systems, structure elasticizing agents, thickeners/structurants, fabric softeners, carriers, hydrotropes, processing aids and/or pigments. However, when one or more adjuncts is present, such one or more adjuncts may be present as detailed below:

Surfactants—The compositions according to the present invention can comprise a surfactant or surfactant system wherein the surfactant can be selected from nonionic and/or anionic and/or cationic surfactants and/or ampholytic and/or zwitterionic and/or semi-polar nonionic surfactants. The surfactant is typically present at a level of from about 0.1%, from about 1%, or even from about 5% by weight of the cleaning compositions to about 99.9%, to about 80%, to about 35%, or even to about 30% by weight of the cleaning compositions.

Builders—The compositions of the present invention can comprise one or more detergent builders or builder systems. When present, the compositions will typically comprise at least about 1% builder, or from about 5% or 10% to about 80%, 50%, or even 30% by weight, of said builder. Builders include, but are not limited to, the alkali metal, ammonium and alkanolammonium salts of polyphosphates, alkali metal silicates, alkaline earth and alkali metal carbonates, aluminosilicate builders polycarboxylate compounds. ether hydroxypolycarboxylates, copolymers of maleic anhydride with ethylene or vinyl methyl ether, 1,3,5-trihydroxybenzene-2,4,6-trisulphonic acid, and carboxymethyl-oxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Chelating Agents—The compositions herein may also optionally contain one or more copper, iron and/or manganese chelating agents. If utilized, chelating agents will generally comprise from about 0.1% by weight of the compositions herein to about 15%, or even from about 3.0% to about 15% by weight of the compositions herein.

Dye Transfer Inhibiting Agents—The compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in the compositions herein, the dye transfer inhibiting agents are present at levels from about 0.0001%, from about 0.01%, from about 0.05% by weight of the cleaning compositions to about 10%, about 2%, or even about 1% by weight of the cleaning compositions.

Dispersants—The compositions of the present invention can also contain dispersants. Suitable water-soluble organic materials are the homo- or co-polymeric acids or their salts, in which the polycarboxylic acid may comprise at least two carboxyl radicals separated from each other by not more than two carbon atoms.

Enzymes—The compositions can comprise one or more detergent enzymes which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. A typical combination is a cocktail of conventional applicable enzymes like protease, lipase, cutinase and/or cellulase in conjunction with amylase.

Enzyme Stabilizers—Enzymes for use in compositions, for example, detergents can be stabilized by various techniques. The enzymes employed herein can be stabilized by the presence of water-soluble sources of calcium and/or magnesium ions in the finished compositions that provide such ions to the enzymes.

Catalytic Metal Complexes—Applicants' compositions may include catalytic metal complexes. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra (methyl-enephosphonic acid) and water-soluble salts thereof. Such catalysts are disclosed in U.S. Pat. No. 4,430,243.

If desired, the compositions herein can be catalyzed by means of a manganese compound. Such compounds and levels of use are well known in the art and include, for example, the manganese-based catalysts disclosed in U.S. Pat. No. 5,576,282.

Cobalt bleach catalysts useful herein are known, and are described, for example, in U.S. Pat. Nos. 5,597,936 and 5,595,967. Such cobalt catalysts are readily prepared by known procedures, such as taught for example in U.S. Pat. Nos. 5,597,936, and 5,595,967.

Compositions herein may also suitably include a transition metal complex of a macropolycyclic rigid ligand—abbreviated as "MRL". As a practical matter, and not by way of limitation, the compositions and cleaning processes herein can be adjusted to provide on the order of at least one part per hundred million of the benefit agent MRL species in the aqueous washing medium, and may provide from about 0.005 ppm to about 25 ppm, from about 0.05 ppm to about 10 ppm, or even from about 0.1 ppm to about 5 ppm, of the MRL in the wash liquor.

Preferred transition-metals in the instant transition-metal bleach catalyst include manganese, iron and chromium. Preferred MRL's herein are a special type of ultra-rigid ligand that is cross-bridged such as 5,12-diethyl-1,5,8,12-tetraazabicyclo[6.6.2]hexa-decane.

Suitable transition metal MRLs are readily prepared by known procedures, such as taught for example in WO 00/32601, and U.S. Pat. No. 6,225,464.

Rheology Modifier

The liquid compositions of the present invention may comprise a rheology modifier. The rheology modifier may be selected from the group consisting of non-polymeric crystalline, hydroxy-functional materials, polymeric rheology modifiers which impart shear thinning characteristics to the aqueous liquid matrix of the composition. In one aspect, such rheology modifiers impart to the aqueous liquid composition a high shear viscosity, at 20 sec$^{-1}$ shear rate and at 21° C., of from 1 to 7000 cps and a viscosity at low shear (0.5 sec$^{-1}$ shear rate at 21° C.) of greater than 1000 cps, or even 1000 cps to 200,000 cps. In one aspect, for cleaning and treatment compositions, such rheology modifiers impart to the aqueous liquid composition a high shear viscosity, at 20 sec$^{-1}$ and at 21° C., of from 50 to 3000 cps and a viscosity at low shear (0.5 sec$^{-1}$ shear rate at 21° C.) of greater than 1000 cps, or even 1000 cps to 200,000 cps. Viscosity according to the present invention is measured using an AR 2000 rheometer from TA instruments using a plate steel spindle having a plate diameter of 40 mm and a gap size of 500 μm. The high shear viscosity at 20 sec$^{-1}$ and low shear viscosity at 0.5 sec$^{-1}$ can be obtained from a logarithmic shear rate sweep from 0.1 sec$^{-1}$ to 25 sec$^{-1}$ in 3 minutes time at 21° C. Crystalline hydroxyl functional materials are rheology modifiers which form thread-like structuring systems throughout the matrix of the composition upon in situ crystallization in the matrix. Polymeric rheology modifiers are preferably selected from polyacrylates, polymeric gums, other non-gum polysaccharides, and combinations of these polymeric materials.

Generally the rheology modifier will comprise from 0.01% to 1% by weight, preferably from 0.05% to 0.75% by weight, more preferably from 0.1% to 0.5% by weight, of the compositions herein.

Structuring agents which are especially useful in the compositions of the present invention may comprise non-polymeric (except for conventional alkoxylation), crystalline hydroxy-functional materials which can form thread-like structuring systems throughout the liquid matrix when they are crystallized within the matrix in situ. Such materials can be generally characterized as crystalline, hydroxyl-containing fatty acids, fatty esters or fatty waxes. In one aspect, rheology modifiers include crystalline, hydroxyl-containing rheology modifiers include castor oil and its derivatives. In one aspect, rheology modifiers include may be hydrogenated castor oil derivatives such as hydrogenated castor oil and hydrogenated castor wax. Commercially available, castor oil-based, crystalline, hydroxyl-containing rheology modifiers include THIXCIN™ from Rheox, Inc. (now Elementis).

Other types of rheology modifiers, besides the non-polymeric, crystalline, hydroxyl-containing rheology modifiers described heretofore, may be utilized in the liquid detergent compositions herein. Polymeric materials which provide shear-thinning characteristics to the aqueous liquid matrix may also be employed.

Suitable polymeric rheology modifiers include those of the polyacrylate, polysaccharide or polysaccharide derivative type. Polysaccharide derivatives typically used as rheology modifiers comprise polymeric gum materials. Such gums include pectine, alginate, arabinogalactan (gum Arabic), carrageenan, gellan gum, xanthan gum and guar gum.

If polymeric rheology modifiers are employed herein, a preferred material of this type is gellan gum. Gellan gum is a heteropolysaccharide prepared by fermentation of Pseudomonaselodea ATCC 31461. Gellan gum is commercially marketed by CP Kelco U.S., Inc. under the KELCO-GEL tradename.

A further alternative and suitable rheology modifier include a combination of a solvent and a polycarboxylate polymer. More specifically the solvent may be an alkylene glycol. In one aspect, the solvent may comprise dipropylene glycol. In one aspect, the polycarboxylate polymer may comprise a polyacrylate, polymethacrylate or mixtures thereof. In one aspect, solvent may be present, based on total composition weight, at a level of from 0.5% to 15%, or from 2% to 9% of the composition. In one aspect, polycarboxylate polymer may be present, based on total composition weight, at a level of from 0.1% to 10%, or from 2% to 5%. In one aspect, the may comprise mixture of dipropylene glycol and 1,2-propanediol. In one solvent component aspect, the ratio of dipropylene glycol to 1,2-propanediol may be 3:1 to 1:3, or even 1:1. In one aspect, the polyacrylate may comprise a copolymer of unsaturated mono- or di-carbonic acid and $C_1$-$C_{30}$ alkyl ester of the (meth) acrylic acid. In another aspect, the rheology modifier may comprise a polyacrylate of unsaturated mono- or di-carbonic acid and $C_1$-$C_{30}$ alkyl ester of the (meth) acrylic acid. Such copolymers are available from Noveon Inc under the tradename Carbopol Aqua 30®.

In the absence of rheology modifier and in order to impart the desired shear thinning characteristics to the liquid composition, the liquid composition can be internally structured through surfactant phase chemistry or gel phases.

Processes of Making and Using Consumer Products

The embodiments of consumer products of the present invention can be formulated into any suitable form and prepared by any process chosen by the formulator, non-limiting examples of which are described in U.S. Pat. No. 5,879,584; U.S. Pat. No. 5,691,297; U.S. Pat. No. 5,574,005; U.S. Pat. No. 5,569,645; U.S. Pat. No. 5,565,422; U.S. Pat. No. 5,516,448; U.S. Pat. No. 5,489,392; U.S. Pat. No. 5,486,303 all of which are incorporated herein by reference.

Method of Use

Compositions, such as consumer products, containing the encapsulate disclosed herein can be used to clean or treat a situs inter alia a surface or fabric. Typically at least a portion of the situs is contacted with an embodiment of Applicants' composition, in neat form or diluted in a liquor, for example, a wash liquor and then the situs may be optionally washed and/or rinsed. In one aspect, a situs is optionally washed and/or rinsed, contacted with an encapsulate according to the present invention or composition comprising said encapsulate and then optionally washed and/or rinsed. For purposes of the present invention, washing includes but is not limited to, scrubbing, and mechanical agitation. The situs may comprise most any material, for example a fabric, fabric capable of being laundered or treated in normal consumer use conditions. Liquors that may comprise the disclosed compositions may have a pH of from about 3 to about 11.5. Such compositions are typically employed at concentrations of from about 500 ppm to about 15,000 ppm in solution. When the wash solvent is water, the water temperature typically ranges from about 5° C. to about 90° C. and, when the situs comprises a fabric, the water to fabric ratio is typically from about 1:1 to about 30:1.

Test Methods

It is understood that the test methods that are disclosed in the Test Methods Section of the present application should be used to determine the respective values of the parameters of Applicants' invention as such invention is described and claimed herein.

Perfume Evaluation Test

1) The test is a 2 product test only A vs B since we compare the performance on soiled garments which have been divided in two.

2) Use a soiled load comprised of dirty/heavily soiled items obtained from consumers and divide each garment in two.

Machine A is filled with 4 half pillowcases 4 half hand towels 4 half dish towels 4 half T-shirts Machine B is filled with the corresponding halves of the garments in Machine A.

3) No suds suppressor is added in this test.

4) The two halves of each garment are graded versus one another for a) perfume impact on a +10/−10 scale b) presence of malodour (on a 0-4 scale—where 0=no malodour and 4=very strong malodour) and c) perfume character on A-D scale where A=no change, B=slight change, C=change, D=significant change. We typically consider perfume impact as the key measure.

EXAMPLES

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

Example 1

Perfumes A-L that provide improved perfume performance under high soil conditions and in cold water washing. Such perfumes are tested in accordance with the Perfume Evaluation Test Method of the present specification and the test results show that such perfumes provide superior performance.

TABLE 1

| PRM No. | A | B | C | D | E | F | G | H | I | J | K | L |
|---|---|---|---|---|---|---|---|---|---|---|---|---|
| 1 | | | | | | | | | | | | |
| 2 | 3.5 | | | | | | | | | | | |
| 3 | 3.5 | | | | | | | | | | | 2.3 |
| 4 | | | | | | 3.6 | | | | | | |
| 5 | | | | | | | | | | | | |
| 6 | | | | | | | | | | | | |
| 7 | | | | | | | | | | | | |
| 8 | | | | | | | | | | | | |
| 9 | | | | | | | | | | | | |
| 10 | | | | | | | | | | | | |
| 11 | 12.5 | 3.5 | | | | | | 1.5 | | | 3.6 | |
| 12 | | | | | | | | | | | | |
| 13 | | | | | | | | | | | | |
| 14 | | | | | | | | | | | | |
| 15 | | | | | | | | | | | | |
| 16 | | | | | | | | 3.5 | | | | |
| 17 | | | | 2.0 | | | 2.0 | | | | | |
| 18 | | | | 1.8 | | | | | | 2.0 | | |
| 19 | | | | | | | | | | | | |
| 20 | | | | | | | | | | | | |
| 21 | | | | | | | | | | | | |
| 22 | | | | | | | | | | | 1.8 | |
| 23 | | | | | | | | | | | | |
| 24 | | | | 3.2 | | | 3.8 | | | | | |
| 25 | | | | | | | | | | | | |
| 26 | | | | | | | 13.0 | | | | | |
| 27 | | | | | | | | | | | | |
| 28 | | | 14 | | | | | | | | | |
| 29 | | | | | | | | | | | | |
| 30 | | | | | | | | | | | | |
| 31 | | | | 13 | | | | | | | | |
| 32 | | | 1.8 | | | 3.5 | | | | | | |
| 33 | | | 8.6 | | | 12.5 | | | | | | |
| 34 | | | | | | | | | | 8.6 | | |
| 35 | | | | | 4.3 | | | | | | | |
| 36 | | | | 9 | | | | | | | | |
| 37 | | | 3.5 | | | | 4.0 | | | | | |
| 38 | | | 1.5 | | | | | | | | | |
| 39 | | | | | | | | | | 13 | | |
| 40 | | | | | | | | | | | 12.8 | |
| 41 | | | | | | | | | | | | |
| 42 | | | | | 4.0 | | | | | | | |
| 43 | | | | | | 1.8 | | | | 3.8 | | |
| 44 | | | 3 | | | | | 3.6 | 2.3 | | | |
| 45 | | | 2 | | | | | | | | | |
| 46 | | | | | | | | | | | | |
| 47 | | | | | | | | | | | | |
| 48 | | | | | | | | | | | | |
| 49 | 1.8 | | | | | | | | | | | 1.5 |
| 50 | | | | | 2.3 | | | | | | 1.8 | |
| 51 | | | | | | | 2.0 | | | | | |
| 52 | | | | | | | | 1.7 | | | | |
| 53 | | | | | | 1.8 | | | | 5.0 | | |
| 54 | | | | | | | | | | | | |
| 55 | | | | | | | | | | | | |
| 56 | | | | | | | | | | | | |
| 57 | | | | | | | | | | | | |
| 58 | | | | 4 | | | | 12.5 | | | | |
| 59 | | | | | | | | | | | 2.0 | |
| 60 | | | | | | 5.2 | | | | | | |
| 61 | | | | | | | 5.4 | | | 5.1 | | |
| 62 | 3.5 | | | | | | | | | | 3.5 | |
| 63 | 3.5 | | | | | | | | | | | |
| 64 | 5.2 | | 3.5 | | | | | | | | | |
| 65 | | | | | | | 5.5 | | | | | |
| 66 | 1.7 | | | | | | | 5.3 | | | 1.6 | 3.5 |
| 67 | | | | 4 | | | 3.6 | | | | | |
| 68 | | | 3.5 | | 2.4 | | | | | 3.3 | | |
| 69 | | | | 3.2 | | 3.5 | | | | | | |
| 70 | | | 1.7 | | | | | | | 1.6 | | |
| 71 | | | | | | | | | | 4.0 | 5.1 | |
| 72 | | | | 5 | | 1.7 | | | | | | |
| 73 | | | 3.5 | | | | | 3.5 | | | | |
| 74 | | | | | | | | 8.9 | | | | |
| 75 | | | | | | | | | | 1.9 | 3.3 | |
| 76 | 8.6 | 3.6 | | | | | | | | | | 2.4 |
| 77 | | 3.2 | | | | 3.5 | | 1.7 | | | | |

TABLE 1-continued

| PRM No. | A | B | C | D | E | F | G | H | I | J | K | L |
|---|---|---|---|---|---|---|---|---|---|---|---|---|
| 78 | | | | | | | | | | | 5.2 | |
| 79 | | | | | | | | | 3.5 | | 8.5 | |
| 80 | | | | | | | | | | | | |
| 81 | | | | | | 8.8 | | | | | | |
| 82 | | 5.2 | | 5.4 | | | | | 3.5 | | 5.4 | |
| 83 | | | 2 | | | | 1.6 | 3.8 | | | | |
| 84 | | 2.8 | 5.5 | 1.3 | | | | | | | | |
| 85 | | | | | | | 0.04 | | | | | |
| 86 | | | | | | 3.2 | | | | | | |
| 87 | 5.2 | | | | | | | | | | | 2.0 |
| 88 | | | | | | | | 8.6 | | | | |
| 89 | | | | | 1.7 | | | | | | | |
| 90 | | | | | | | | | 0.05 | | | |
| 91 | 1.7 | 8.0 | | | | | | | 2.0 | | | |
| 92 | | | | | | | | 5.3 | | | | |
| 93 | | | | 1.6 | | | | | 1.8 | | | |
| 94 | | | | 5.0 | | | 1.8 | | 2.5 | | | |
| 95 | | | | | | | | | | 0.05 | | |
| 96 | | | | 0.04 | | 0.05 | | | | | | |
| 97 | | | 0.07 | | | | | | | 0.03 | | |
| 98 | 0.05 | | | | | | | | | | | |
| 99 | | | | | 3.2 | | | | 2.3 | | | |
| 100 | | | | | | 5.3 | 3.6 | | | | | |
| 101 | | 7.2 | | | | | | | | | | 0.5 |
| 102 | | | | | | | | | 3.5 | | | |
| 103 | | | | | | | | | | | | |
| 104 | | | | | | | | | | 5.5 | 3.6 | |
| 105 | | 3.2 | | 1.8 | | | | | 2.3 | | | 2.0 |
| 106 | | 10.0 | | | | | | | | | | 4.0 |
| 107 | | 2.2 | | | 3.5 | | | | 1.8 | | | 2.0 |
| 108 | | 4.5 | | | 3.6 | | | | 1.8 | | | 1.2 |
| 109 | | | | | | | | | | | | 4.0 |
| 110 | | 7.8 | | | 2.3 | | | | 5.6 | | | 1.8 |
| 111 | | 4.3 | | 1.6 | | | | | 3.4 | | | 2.1 |
| 112 | | 1.8 | | | 3.1 | | | | 2.5 | | | 0.8 |
| 113 | | 1.5 | | | | | | | | | | 3.4 |
| 114 | | | 1.3 | | 1.5 | | 3.2 | | 1.2 | 1.7 | | |
| 115 | | 1.4 | | | | | | | | | | 3.1 |

Example 2

84 wt % Core/16 wt % Wall Melamine Formaldehyde (MF) Capsule 25 grams of butyl acrylate-acrylic acid copolymer emulsifier (Colloid C351, 25% solids, pka 4.5-4.7, (Kemira Chemicals, Inc. Kennesaw, Ga. U.S.A.) is dissolved and mixed in 200 grams deionized water. The pH of the solution is adjusted to pH of 4.0 with sodium hydroxide solution. 8 grams of partially methylated methylol melamine resin (Cymel 385, 80% solids, (Cytec Industries West Paterson, N.J., U.S.A.)) is added to the emulsifier solution. 200 grams of perfume oil is added to the previous mixture under mechanical agitation and the temperature is raised to 50° C. After mixing at higher speed until a stable emulsion is obtained, the second solution and 4 grams of sodium sulfate salt are added to the emulsion. This second solution contains 10 grams of butyl acrylate-acrylic acid copolymer emulsifier (Colloid C351, 25% solids, pka 4.5-4.7, Kemira), 120 grams of distilled water, sodium hydroxide solution to adjust pH to 4.8, 25 grams of partially methylated methylol melamine resin (Cymel 385, 80% solids, Cytec). This mixture is heated to 70° C. and maintained overnight with continuous stifling to complete the encapsulation process. 23 grams of acetoacetamide (Sigma-Aldrich, Saint Louis, Mo., U.S.A.) is added to the suspension. An average capsule size of 30 um is obtained as analyzed by a Model 780 Accusizer.

Example 3

80 wt % Core/20 wt % Wall Melamine Formaldehyde Capsule 18 grams of a blend of 50% butyl acrylate-acrylic acid copolymer emulsifier (Colloid C351, 25% solids, pka 4.5-4.7, Kemira) and 50% polyacrylic acid (35% solids, pKa 1.5-2.5, Aldrich) is dissolved and mixed in 200 grams deionized water. The pH of the solution is adjusted to pH of 3.5 with sodium hydroxide solution. 6.5 grams of partially methylated methylol melamine resin (Cymel 385, 80% solids Cytec) is added to the emulsifier solution. 200 grams of perfume oil is added to the previous mixture under mechanical agitation and the temperature is raised to 60° C. After mixing at higher speed until a stable emulsion is obtained, the second solution and 3.5 grams of sodium sulfate salt are poured into the emulsion. This second solution contains 10 grams of butyl acrylate-acrylic acid copolymer emulsifier (Colloid C351, 25% solids, pka 4.5-4.7, Kemira), 120 grams of distilled water, sodium hydroxide solution to adjust pH to 4.6, 30 grams of partially methylated methylol melamine resin (Cymel 385, 80% Cytec). This mixture is heated to 75° C. and maintained 6 hours with continuous stirring to complete the encapsulation process. 23 grams of acetoacetamide (Sigma-Aldrich, Saint Louis, Mo., U.S.A.) is added to the suspension.

Example 4

80 wt % Core/20 wt % Melamine Formaldehyde Wall Capsule 36 grams of butyl acrylate-acrylic acid copolymer emulsifier (Colloid C351, 25% solids, pKa 4.5-4.7, Kemira) is dissolved and mixed in 200 grams deionized water. The pH of the solution is adjusted to pH of 5.0 with sodium hydroxide solution. 12 grams of partially methylated methylol melamine resin (Cymel 385, 80% solids, Cytec) is added to the emulsifier solution. 200 grams of perfume oil is added to the previous mixture under mechanical agitation and the temperature is raised to 65° C. After mixing at higher speed until a stable emulsion is obtained, the second solution and 5 grams of sodium sulfate salt are added to the emulsion. This second solution contains 12 grams of butyl acrylate-acrylic acid copolymer emulsifier (Colloid C351, 25% solids, pKa 4.5-4.7, Kemira), 120 grams of distilled water, sodium hydroxide solution to adjust pH to 5, 33 grams of partially methylated methylol melamine resin (Cymel 385, 80% solids, Cytec). This mixture is heated to 65° C. and maintained overnight with continuous stirring to complete the encapsulation process. 23 grams of acetoacetamide (Sigma-Aldrich, Saint Louis, Mo., U.S.A.) is added to the suspension.

Example 5

80 wt % Core/20 wt % Wall Melamine Formaldehyde Capsule 20 grams of butyl acrylate-acrylic acid copolymer emulsifier (Colloid C351, 25% solids, pKa 4.5-4.7, Kemira) is dissolved and mixed in 200 grams deionized water. The pH of the solution is adjusted to pH of 5.5 with sodium hydroxide solution. 6 grams of partially methylated methylol melamine resin (Cymel 385, 80% solids, Cytec) is added to the emulsifier solution. 200 grams of perfume oil is added to the previous mixture under mechanical agitation and the temperature is raised to 55° C. After mixing at higher speed until a stable emulsion is obtained, the second solution and 9 grams of sodium sulfate salt is added to the emulsion. This second solution contains 8 grams of polyacrylic acid (35% solids, pka 1.5-2.5, Aldrich), 120 grams of distilled water, sodium hydroxide solution to adjust pH to 4.4, 35 grams of partially methylated methylol melamine resin (Cymel 385, 80% solids, Cytec). This mixture is heated to 80° C. and maintained 4 hours with continuous stifling to complete the encapsulation process. 23 grams of acetoacetamide (Sigma-Aldrich, Saint Louis, Mo., U.S.A.) is added to the suspension.

Example 6

Melamine Formaldehyde Capsule

The composition of and the procedures for preparing the capsules are the same composition as in Example 5 except for the following: the melamine formaldehyde resin is a mix of 80% partially methylated methylol melamine resin and 20% of fully methylated melamine resin.

Example 7

Melamine Formaldehyde Capsule

The procedure for preparing the capsules is the same as in Example 5, except for the following compositional changes to the perfume emulsification liquor (the first solution):

| Material | A | B | C | D | E | F | G |
|---|---|---|---|---|---|---|---|
| Copolymer of Polyacrylic Acid-Butyl Acrylate | 42 | 31 | 0 | 20 | 26 | 18 | 0 |
| Polyacrylic Acid | 0 | 21 | 29 | 14 | 0 | 22 | 27 |
| 20% NaOH | 2 | 3 | 6 | 9 | 2 | 7 | 7 |
| Melamine Resin | 19 | 21 | 21 | 8 | 4 | 7 | 17 |
| Perfume Oil | 265 | 290 | 246 | 224 | 220 | 200 | 204 |
| Water | 95 | 104 | 103 | 225 | 159 | 189 | 237 |

The procedure for preparing the capsules is the same as in Example 4, except for the following compositional changes to the second solution:

| Material | A | B | C | D | E | F | G |
|---|---|---|---|---|---|---|---|
| Copolymer of Polyacrylic Acid-Butyl Acrylate | 11 | 0 | 15 | 0 | 0 | 3 | 3 |
| Polyacrylic Acid | 11 | 12 | 0 | 4 | 9 | 8 | 10 |
| 20% NaOH | 0.4 | 0.4 | 0.1 | 0.3 | 0.4 | 0.4 | 0.4 |
| Melamine Resin | 8 | 4 | 16 | 13 | 26 | 23 | 29 |
| Water | 115 | 126 | 43 | 147 | 52 | 47 | 78 |

Followed by the addition of acetoacetamide at a level of 5 wt % of the weight of the batch.

Example 8

Melamine Formaldehyde Capsule

The composition of and the procedures for preparing the capsules are the same composition as in Example 5 except for the following: 0.7% of ammonium hydroxide is added to the suspension instead of acetoacetamide.

Example 9

Wall Melamine Formaldehyde (MF) perfume Capsule with high core density ($\geq 1$) 25 grams of butyl acrylate-acrylic acid copolymer emulsifier (Colloid C351, 25% solids, pka 4.5-4.7, (Kemira Chemicals, Inc. Kennesaw, Ga. U.S.A.) is dissolved and mixed in 200 grams deionized water. The pH of the solution is adjusted to pH of 5.0 with sodium hydroxide solution. 5 grams of partially methylated methylol melamine resin (Cymel 385, 80% solids, (Cytec Industries West Paterson, N.J., U.S.A.)) is added to the emulsifier solution. 150 grams of perfume oil and 50 grams of Brominated Vegetable oil (d=1.3; Virginia Dare, Brooklyn, N.Y., USA) are added to the previous mixture under mechanical agitation and the temperature is raised to 50° C. After mixing at higher speed until a stable emulsion is obtained, the second solution and 4 grams of sodium sulfate salt are added to the emulsion. This second solution contains 10 grams of butyl acrylate-acrylic acid copolymer emulsifier (Colloid C351, 25% solids, pka 4.5-4.7, Kemira), 120 grams of distilled water, sodium hydroxide solution to adjust pH to 4.8, 25 grams of partially methylated methylol melamine resin (Cymel 385, 80% solids, Cytec). This mixture is heated to 70° C. and maintained overnight with continuous stifling to complete the encapsulation process. 23 grams of acetoacetamide (Sigma-Aldrich, Saint Louis, Mo., U.S.A.) is added to the suspension. An average capsule size of 30 um is obtained as analyzed by a Model 780 Accusizer.

Example 10

Production of Spray Dried Microcapsule 1200 g of perfume microcapsule slurry, containing one or more of the variants of microcapsules disclosed in the present specification, is mixed together with 700 g of water for 10 minutes using an IKA Eurostar mixer with R1382 attachment at a speed of 180 rpm. The mixture is then transferred over to a feeding vessel to be spray dried in a 1.2 m diameter Niro Production Minor. The slurry is fed into the tower using a Watson-Marlow 504U peristaltic pump and atomised using a 100 mm diameter rotary atomiser run at 18000 rpm, with co-current air flow for drying. The slurry is dried using an inlet temperature of 200° C. and outlet temperature of 95° C. to form a fine powder. The equipment used the spray drying process may be obtained from the following suppliers: IKA Werke GmbH & Co. KG, Janke and Kunkel—Str. 10, D79219 Staufen, Germany; Niro A/S Gladsaxevej 305, P.O. Box 45, 2860 Soeborg, Denmark and Watson-Marlow Bredel Pumps Limited, Falmouth, Cornwall, TR11 4RU, England.

Example 11

To demonstrate the benefit of the present invention, Applicants prepared liquid detergent matrix A, below.

| Active Material in weight % | A |
|---|---|
| $C_{14}$-$C_{15}$ alkyl poly ethoxylate 7 | 3.39 |
| $C_{12}$-$C_{14}$ alkyl poly ethoxylate 7 | 1.13 |
| $C_{12}$-$C_{14}$ alkyl poly ethoxylate 3 sulfate Na salt | 7.66 |
| Alkylbenzene sulfonic acid | 1.17 |
| Citric Acid | 2.73 |
| $C_{12-18}$ fatty acid | 5.06 |
| Enzymes | 0.2 |
| Boric Acid | 1.40 |
| Trans-sulphated ethoxylated hexamethylene diamine quat | 0.81 |
| Diethylene triamine penta methylene phosphonic acid | 0.12 |
| Hydrogenated Castor Oil structurant | 0.300 |
| Ethanol | 1.59 |
| 1,2 propanediol | 0.07 |
| Sodium hydroxide | 3.48 |
| Silicone PDMS emulsion | 0.0025 |
| Blue Dye | 0.0006 |
| Preservative Acticide MBS 2550 (ex Thor) | 0.0135 |
| Perfume | Nil |
| Merquat 5300 polymer (1) | 0.19 |
| Water | Up to 95% |

| | A1 | A2 | A3 | A4 | A5 | A6 | A7 | A8 | A9 |
|---|---|---|---|---|---|---|---|---|---|
| Scavenger 1 Acetoacetamide | — | — | 0.035% | 0.035% | 0.035% | 0.035% | 0.035% | 0.035% | 0.035% |
| Scavenger 2 K-sulphite | — | — | — | — | — | — | 0.1 | 0.2 | 0.2 |
| PMCs from Example 2 | — | 0.3 | 0.3 | 0.3 | — | — | 0.3 | 0.3 | — |
| PMCs from Example 3 | | | | | | | | | |
| PMCs from Example 4 | — | — | — | — | 0.3 | 0.3 | — | — | 0.3 |
| Perfume | — | — | — | 0.6 | — | 0.6 | 0.6 | 0.6 | — |
| Water | Up to 100 | Up to 100 | Up to 100 | Up to 100 | Up to 100 | Up to 100 | Up to 100 | Up to 100 | Up to 100 |

(1) Merquat 5300: terpolymer with mole ratio: 90% PAM/5% AA/5% MAPTAC produced by Nalco.

Examples 12-19

Examples of laundry detergent compositions comprising the perfume composition are included below.

| | % w/w of laundry detergent compositions | | | | | | | |
|---|---|---|---|---|---|---|---|---|
| Raw material | 12 | 13 | 14 | 15 | 16 | 17 | 18 | 19 |
| Linear alkyl benzene sulphonate | 7.1 | 6.7 | 11.0 | 10.6 | 6.9 | 4.5 | 10.1 | 8.9 |
| Sodium $C_{12-15}$ alkyl ethoxy sulphate having a molar average degree of ethoxylation of 3 | 3.5 | 0.0 | 1.5 | 0.0 | 0.0 | 0.0 | 0.0 | 1.9 |
| Acrylic Acid/Maleic Acid Copolymer | 3.6 | 1.8 | 4.9 | 2.0 | 1.0 | 1.6 | 3.9 | 2.3 |
| Sodium Alumino Silicate (Zeolite 4A) | 4.0 | 0.5 | 0.8 | 1.4 | 16.3 | 0.0 | 17.9 | 2.4 |

-continued

| Raw material | \% w/w of laundry detergent compositions | | | | | | | |
|---|---|---|---|---|---|---|---|---|
| | 12 | 13 | 14 | 15 | 16 | 17 | 18 | 19 |
| Sodium Tripolyphosphate | 0.0 | 17.5 | 0.0 | 15.8 | 0.0 | 23.3 | 0.0 | 0.0 |
| Sodium Carbonate | 23.2 | 16.8 | 30.2 | 17.3 | 18.4 | 9.0 | 20.8 | 30.0 |
| Sodium Sulphate | 31.4 | 29.4 | 35.5 | 7.2 | 26.3 | 42.8 | 33.2 | 28.3 |
| Sodium Silicate | 0.0 | 4.4 | 0.0 | 4.5 | 0.0 | 6.1 | 0.0 | 4.6 |
| $C_{14-15}$ alkyl ethoxylated alcohol having a molar average degree of ethoxylation of 7 | 0.4 | 2.6 | 0.8 | 2.5 | 3.1 | 0.3 | 3.8 | 0.4 |
| Sodium Percarbonate | 16.0 | 0.0 | 8.4 | 20.4 | 13.1 | 3.6 | 0.0 | 7.0 |
| Sodium Perborate | 0.0 | 9.9 | 0.0 | 0.0 | 0.0 | 0.0 | 0.0 | 0.0 |
| Tetraacetylethylenediamine (TAED) | 2.2 | 1.7 | 0.0 | 4.7 | 3.6 | 0.0 | 0.0 | 0.8 |
| Calcium Bentonite | 0.0 | 0.0 | 0.0 | 1.8 | 0.0 | 0.0 | 0.0 | 5.6 |
| Citric acid | 2.0 | 1.5 | 2.0 | 2.0 | 2.5 | 1.0 | 2.5 | 1.0 |
| Protease (84 mg active/g) | 0.14 | 0.12 | 0.0 | 0.12 | 0.09 | 0.08 | 0.10 | 0.08 |
| Amylase (22 mg active/g) | 0.10 | 0.11 | 0.0 | 0.10 | 0.10 | 0.0 | 0.14 | 0.08 |
| Lipase (11 mg active/g) | 0.70 | 0.50 | 0.0 | 0.70 | 0.50 | 0.0 | 0.0 | 0.0 |
| Cellulase (2.3 mg active/g) | 0.0 | 0.0 | 0.0 | 0.0 | 0.0 | 0.0 | 0.18 | 0.0 |
| Benefit agent composition of Example 10 | 1.4 | 0.6 | 0.8 | 1.0 | 0.7 | 0.3 | 0.7 | 1.2 |
| Water & Miscellaneous | Balance to 100% | | | | | | | |

Examples 20-27

Examples of granular laundry detergent compositions comprising the perfume composition are included below.

| Raw material | \% w/w of laundry detergent compositions | | | | | | | |
|---|---|---|---|---|---|---|---|---|
| | 20 | 21 | 22 | 23 | 24 | 25 | 26 | 27 |
| Linear alkyl benzene sulphonate | 7.1 | 6.7 | 11.0 | 10.6 | 6.9 | 4.5 | 10.1 | 8.9 |
| Sodium $C_{12-15}$ alkyl ethoxy sulphate having a molar average degree of ethoxylation of 3 | 3.5 | 0.0 | 1.5 | 0.0 | 0.0 | 0.0 | 0.0 | 1.9 |
| Acrylic Acid/Maleic Acid Copolymer | 3.6 | 1.8 | 4.9 | 2.0 | 1.0 | 1.6 | 3.9 | 2.3 |
| Sodium Alumino Silicate (Zeolite 4A) | 4.0 | 0.5 | 0.8 | 1.4 | 16.3 | 0.0 | 17.9 | 2.4 |
| Sodium Tripolyphosphate | 0.0 | 17.5 | 0.0 | 15.8 | 0.0 | 23.3 | 0.0 | 0.0 |
| Sodium Carbonate | 23.2 | 16.8 | 30.2 | 17.3 | 18.4 | 9.0 | 20.8 | 30.0 |
| Sodium Sulphate | 31.4 | 29.4 | 35.5 | 7.2 | 26.3 | 42.8 | 33.2 | 28.3 |
| Sodium Silicate | 0.0 | 4.4 | 0.0 | 4.5 | 0.0 | 6.1 | 0.0 | 4.6 |
| $C_{14-15}$ alkyl ethoxylated alcohol having a molar average degree of ethoxylation of 7 | 0.4 | 2.6 | 0.8 | 2.5 | 3.1 | 0.3 | 3.8 | 0.4 |
| Sodium Percarbonate | 16.0 | 0.0 | 8.4 | 20.4 | 13.1 | 3.6 | 0.0 | 7.0 |
| Sodium Perborate | 0.0 | 9.9 | 0.0 | 0.0 | 0.0 | 0.0 | 0.0 | 0.0 |
| Tetraacetylethylenediamine (TAED) | 2.2 | 1.7 | 0.0 | 4.7 | 3.6 | 0.0 | 0.0 | 0.8 |
| Calcium Bentonite | 0.0 | 0.0 | 0.0 | 1.8 | 0.0 | 0.0 | 0.0 | 5.6 |
| Citric acid | 2.0 | 1.5 | 2.0 | 2.0 | 2.5 | 1.0 | 2.5 | 1.0 |
| Protease (84 mg active/g) | 0.14 | 0.12 | 0.0 | 0.12 | 0.09 | 0.08 | 0.10 | 0.08 |
| Amylase (22 mg active/g) | 0.10 | 0.11 | 0.0 | 0.10 | 0.10 | 0.0 | 0.14 | 0.08 |
| Lipase (11 mg active/g) | 0.70 | 0.50 | 0.0 | 0.70 | 0.50 | 0.0 | 0.0 | 0.0 |
| Cellulase (2.3 mg active/g) | 0.0 | 0.0 | 0.0 | 0.0 | 0.0 | 0.0 | 0.18 | 0.0 |
| Benefit agent composition of Example 10 | 1.4 | 0.6 | 0.8 | 1.0 | 0.7 | 0.3 | 0.7 | 1.2 |
| Water & Miscellaneous | Balance to 100% | | | | | | | |

The equipment and materials described in Examples 1 through to 19 can be obtained from the following: IKA Werke GmbH & Co. KG, Staufen, Germany; CP Kelco, Atlanta, United States; Forberg International AS, Larvik, Norway; Degussa GmbH, Düsseldorf, Germany; Niro A/S, Soeberg, Denmark; Baker Perkins Ltd, Peterborough, United Kingdom; Nippon Shokubai, Tokyo, Japan; BASF, Ludwigshafen, Germany; Braun, Kronberg, Germany; Industrial Chemicals Limited, Thurrock, United Kingdom; Primex ehf, Siglufjordur, Iceland; ISP World Headquarters; Polysciences, Inc. of Warrington, Pa., United States; Cytec Industries Inc., New Jersey, United States; International Specialty Products, Wayne, N.J., United States; P&G Chemicals Americas, Cincinnati, Ohio, United States; Sigma-Aldrich Corp., St. Louis, Mo., United States, Dow Chemical Company of Midland, Mich., USA Examples 28-37

Fabric Conditioner

Non-limiting examples of fabric conditioners containing the polymer coated perfume microcapsules disclosed in the present specification are summarized in the following table.

|  | EXAMPLES | | | | | | | | | |
|---|---|---|---|---|---|---|---|---|---|---|
| (% wt) | 28 | 29 | 30 | 31 | 32 | 33 | 34 | 35 | 36 | 37 |
| FSA [a] | 14 | 16.47 | 14 | 12 | 12 | 16.47 | — | — | 5 | 10 |
| FSA [b] | — | — | — | — | — | — | 3.00 | — | — | — |
| FSA [c] | — | — | — | — | — | — | — | 6.5 | — | — |
| Ethanol | 2.18 | 2.57 | 2.18 | 1.95 | 1.95 | 2.57 | — | — | 0.81 | — |
| Isopropyl Alcohol | — | — | — | — | — | — | 0.33 | 1.22 | — | 1.0 |
| Starch [d] | 1.25 | 1.47 | 2.00 | 1.25 | — | 2.30 | 0.5 | 0.70 | 0.71 | 0.42 |
| Phase Stabilizing Polymer [f] | 0.21 | 0.25 | 0.21 | 0.21 | 0.14 | 0.18 | 0.15 | 0.14 | 0.2 | 0.1 |
| Suds Suppressor [g] | — | — | — | — | — | — | — | 0.1 | — | — |
| Calcium Chloride | 0.15 | 0.176 | 0.15 | 0.15 | 0.30 | 0.176 | — | 0.1-0.15 | — | 0025. |
| DTPA [h] | 0.017 | 0.017 | 0.017 | 0.017 | 0.007 | 0.007 | 0.20 | — | 0.002 | 0.002 |
| Preservative (ppm) [i,j] | 5 | 5 | 5 | 5 | 5 | 5 | — | 250 [j] | 5 | 5 |
| Antifoam [k] | 0.015 | 0.018 | 0.015 | 0.015 | 0.015 | 0.015 | — | — | 0.015 | 0.015 |
| Dye(ppm) | 40 | 40 | 40 | 40 | 40 | 40 | 11 | 30-300 | 30 | 30 |
| Ammonium Chloride | 0.100 | 0.118 | 0.100 | 0.100 | 0.115 | 0.115 | — | — | — | — |
| HCl | 0.012 | 0.014 | 0.012 | 0.012 | 0.028 | 0.028 | 0.016 | 0.025 | 0.011 | 0.011 |
| Perfume microcapsules as disclosed in Example 2 | 0.2 | 0.02 | 0.1 | 0.15 | 0.12 | 0.13 | 0.3 | 0.4 | 0.24 | 0.1 |
| Additional Neat Perfume | 0.8 | 0.7 | 0.9 | 0.5 | 1.2 | 0.5 | 1.1 | 0.6 | 1.0 | 0.9 |
| Deionized Water | † | † | † | † | † | † | † | † | † | † |

[a] N,N-di(tallowoyloxyethyl)-N,N-dimethylammonium chloride.
[b] Methyl bis (tallow amidoethyl)2-hydroxyethyl ammonium methyl sulfate.
[c] Reaction product of Fatty acid with Methyldiethanolamine in a molar ratio 1.5:1, quaternized with Methylchloride, resulting in a 1:1 molar mixture of N,N-bis(stearoyl-oxy-ethyl) N,N-dimethyl ammonium chloride and N-(stearoyl-oxy-ethyl) N,-hydroxyethyl N,N dimethyl ammonium chloride.
[d] Cationic high amylose maize starch available from National Starch under the trade name CATO ®.
[f] Rheovis DCE ex BASF.
[g] SE39 from Wacker
[h] Diethylenetriaminepentaacetic acid.
[i] KATHON ® CG available from Rohm and Haas Co. "PPM" is "parts per million."
[j] Gluteraldehyde
[k] Silicone antifoam agent available from Dow Corning Corp. under the trade name DC2310.
† balance Examples 38-43

Liquid Laundry Formulations (HDLs)

| Ingredient | 38 | 39 | 40 | 41 | 42 | 43 |
|---|---|---|---|---|---|---|
| Alkyl Ether Sulphate | 0.00 | 0.50 | 12.0 | 12.0 | 6.0 | 7.0 |
| Dodecyl Benzene Sulphonic Acid | 8.0 | 8.0 | 1.0 | 1.0 | 2.0 | 3.0 |
| Ethoxylated Alcohol | 8.0 | 6.0 | 5.0 | 7.0 | 5.0 | 3.0 |
| Citric Acid | 5.0 | 3.0 | 3.0 | 5.0 | 2.0 | 3.0 |
| Fatty Acid | 3.0 | 5.0 | 5.0 | 3.0 | 6.0 | 5.0 |
| Ethoxysulfated hexamethylene diamine quaternized | 1.9 | 1.2 | 1.5 | 2.0 | 1.0 | 1.0 |
| Diethylene triamine penta methylene phosphonic acid | 0.3 | 0.2 | 0.2 | 0.3 | 0.1 | 0.2 |

-continued

| Ingredient | 38 | 39 | 40 | 41 | 42 | 43 |
|---|---|---|---|---|---|---|
| Enzymes | 1.20 | 0.80 | 0 | 1.2 | 0 | 0.8 |
| Brightener (disulphonated diamino stilbene based FWA) | 0.14 | 0.09 | 0 | 0.14 | 0.01 | 0.09 |
| Cationic hydroxyethyl cellulose | 0 | 0 | 0.10 | 0 | 0.200 | 0.30 |
| Poly(acrylamide-co-diallyldimethylammonium chloride) | 0 | 0 | 0 | 0.50 | 0.10 | 0 |
| Hydrogenated Castor Oil Structurant | 0.50 | 0.44 | 0.2 | 0.2 | 0.3 | 0.3 |
| Boric acid | 2.4 | 1.5 | 1.0 | 2.4 | 1.0 | 1.5 |
| Ethanol | 0.50 | 1.0 | 2.0 | 2.0 | 1.0 | 1.0 |
| 1,2 propanediol | 2.0 | 3.0 | 1.0 | 1.0 | 0.01 | 0.01 |
| Glutaraldehyde | 0 | 0 | 19 ppm | 0 | 13 ppm | 0 |
| Diethyleneglycol (DEG) | 1.6 | 0 | 0 | 0 | 0 | 0 |
| 2,3-Methyl-1,3-propanediol (M pdiol) | 1.0 | 1.0 | 0 | 0 | 0 | 0 |
| Mono Ethanol Amine | 1.0 | 0.5 | 0 | 0 | 0 | 0 |
| NaOH Sufficient To Provide Formulation pH of: | pH 8 | pH 8 | pH 8 | pH 8 | pH 8 | pH 8 |
| Sodium Cumene Sulphonate (NaCS) | 2.00 | 0 | 0 | 0 | 0 | 0 |
| Silicone (PDMS) emulsion | 0.003 | 0.003 | 0.003 | 0.003 | 0.003 | 0.003 |
| Neat Perfume | 0.02 | 0.15 | 0.0 | 0.2 | 0.3 | 0.1 |
| Perfume microcapsules as disclosed in Example 2 | 0.2 | 0.02 | 0.1 | 0.15 | 0.12 | 0.13 |
| Water | Balance | Balance | Balance | Balance | Balance | Balance |

Examples 44-51

Liquid Unit Dose

The following are examples of unit dose executions wherein the liquid composition is enclosed within a PVA film. The preferred film used in the present examples is Monosol M8630 76 μm thickness.

| | D 3 compartments | | | E 2 compartments | | F 3 compartments | | |
|---|---|---|---|---|---|---|---|---|
| | Compartment # | | | | | | | |
| | 44 | 45 | 46 | 47 | 48 | 49 | 50 | 51 |
| | Dosage (g) | | | | | | | |
| | 34.0 | 3.5 | 3.5 | 30.0 | 5.0 | 25.0 | 1.5 | 4.0 |
| Ingredients | Weight % | | | | | | | |
| Alkylbenzene sulfonic acid | 20.0 | 20.0 | 20.0 | 10.0 | 20.0 | 20.0 | 25 | 30 |
| Alkyl sulfate | | | | 2.0 | | | | |
| $C_{12-14}$ alkyl 7-ethoxylate | 17.0 | 17.0 | 17.0 | | 17.0 | 17.0 | 15 | 10 |
| $C_{12-14}$ alkyl ethoxy 3 sulfate | 7.5 | 7.5 | 7.5 | | | 7.5 | 7.5 | |
| Citric acid | 0.5 | | 2.0 | 1.0 | | | | 2.0 |
| Zeolite A | | | | 10.0 | | | | |
| $C_{12-18}$ Fatty acid | 13.0 | 13.0 | 13.0 | | 18.0 | 18.0 | 10 | 15 |
| Sodium citrate | | | | 4.0 | 2.5 | | | |
| enzymes | 0-3 | 0-3 | 0-3 | 0-3 | | 0-3 | 0-3 | 0-3 |
| Sodium Percarbonate | | | | 11.0 | | | | |
| TAED | | | | 4.0 | | | | |
| Polycarboxylate | | | | 1.0 | | | | |
| Ethoxylated Polyethylenimine[1] | 2.2 | 2.2 | 2.2 | | | | | |
| Hydroxyethane diphosphonic acid | 0.6 | 0.6 | 0.6 | 0.5 | | | 2.2 | |
| Ethylene diamine tetra(methylene phosphonic) acid | | | | | | 0.4 | | |
| Brightener | 0.2 | 0.2 | 0.2 | 0.3 | | 0.3 | | |

-continued

|  | D<br>3 compartments | | | E<br>2 compartments | | F<br>3 compartments | | |
|---|---|---|---|---|---|---|---|---|
|  | Compartment # | | | | | | | |
|  | 44 | 45 | 46 | 47 | 48 | 49 | 50 | 51 |
|  | Dosage (g) | | | | | | | |
|  | 34.0 | 3.5 | 3.5 | 30.0 | 5.0 | 25.0 | 1.5 | 4.0 |
| Ingredients | Weight % | | | | | | | |
| Perfume Microcapsules as Example2 | 0.4 | 1.2 | 1.5 | 1.3 | 1.3 | 0.4 | 0.12 | 0.2 |
| Water | 9 | 8.5 | 10 | 5 | 11 | 10 | 10 | 9 |
| CaCl2 |  |  |  |  |  |  | 0.01 |  |
| Perfume | 1.7 | 1.7 |  | 0.6 |  | 1.5 | 0.5 |  |
| Minors (antioxidant, sulfite, aesthetics, . . .) | 2.0 | 2.0 | 2.0 | 4.0 | 1.5 | 2.2 | 2.2 | 2.0 |
| Buffers (sodium carbonate, monoethanolamine)[3] | To pH 8.0 for liquids<br>To RA > 5.0 for powders | | | | | | | |
| Solvents (1,2 propanediol, ethanol), Sulfate | To 100 p | | | | | | | |

Polyethylenimine (MW = 600) with 20 ethoxylate groups per —NH.
[3]RA = Reserve Alkalinity (g NaOH/dose)

Example 52

Shampoo Formulation

| Ingredient | |
|---|---|
| Ammonium Laureth Sulfate (AE₃S) | 6.00 |
| Ammonium Lauryl Sulfate (ALS) | 10.00 |
| Laureth-4 Alcohol | 0.90 |
| Trihydroxystearin | 0.10 |
| Polymer coated perfume microcapsules as disclosed in Example 2 | 0.60 |
| Sodium Chloride | 0.40 |
| Citric Acid | 0.04 |
| Sodium Citrate | 0.40 |
| Sodium Benzoate | 0.25 |
| Ethylene Diamine Tetra Acetic Acid | 0.10 |
| Dimethicone | 1.00 |
| Water and Minors (QS to 100%) | Balance |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A perfume comprising, based on total perfume weight:
   a) from 3% to 20% of a perfume raw material selected from the group consisting of 2-methoxynaphthalene, 1,1-diethoxydecane, 1,3,3-trimethyl-2-oxabicyclo[2,2,2]octane and mixtures thereof;
   b) from 2% to 35% of a perfume raw material selected from the group consisting of 3-(4-propan-2-ylphenyl)butanal, 3-(4-tert-butylphenyl)propanal and mixtures thereof;
   c) from 2% to 35% of a perfume raw material selected from the group consisting of propan-2-yl 2-methylbutanoate, ethyl 2-methylbutanoate, ethyl 2-methylpentanoate, hexyl acetate, 5-heptyloxolan-2-one, 2-[2-(4-methyl-1-cyclohex-3-enyl)propyl]cyclopentan-1-one and mixtures thereof;
   d) from 0% to 10% of a perfume raw material selected from the group consisting of (E)-4-methyldec-3-en-5-ol, Cyclopentol, Laevo trisandol, 3,7-dimethylocta-1,6-dien-3-ol and mixtures thereof;
   e) from 0% to 10% of a perfume raw material selected from the group consisting of 2-heptylcyclopentan-1-one, O-[2-[(1S)-4-methyl-2-oxocyclohexyl]propan-2-yl] ethanethioate, 2-[2-(4-methyl-1-cyclohex-3-enyl)propyl]cyclopentan-1-one, naphthalen-2-yl-phenylmethanone, 2-[(2E)-3,7-dimethylocta-2,6-dienyl]cyclopentan-1-one, 2,2,5-trimethyl-5-pentylcyclopentan-1-one, (E)-1-(2,6,6-trimethyl-1-cyclohex-3-enyl)but-2-en-1-one, (E)-3-methyl-4-(2,6,6-trimethyl-1-cyclohex-2-enyl)but-3-en-2-one and mixtures thereof; and
   f) from 0% to 0.5% of a perfume raw material selected from the group consisting of 4-methoxy-2-methylbutane-2-thiol, 2-(4-methyl-1-cyclohex-3-enyl)propane-2-thiol, N-(1,5-dimethyl-8-bicyclo[3.2.1]octanylidene)hydroxylamine, 2,4,4,7-Tetramethyl-6,8-nonadiene-3-one oxime, 2-Methyldecanenitrile, 3a,6,6,9a-tetramethyl-2,4,5,5a,7,8,9,9b-octahydro-1H-benzo[e][1]benzofuran and mixtures thereof.

* * * * *